United States Patent
Hayase et al.

(10) Patent No.: US 6,300,353 B1
(45) Date of Patent: Oct. 9, 2001

(54) AZOLES FOR TREATMENT OF FUNGAL INFECTIONS

(75) Inventors: Tadakatsu Hayase, Chigasaki; Shigeyasu Ichihara, Kawasaki; Yoshiaki Isshiki, Chigasaki; Pingli Liu, Fujisawa; Jun Ohwada, Kamakura; Toshiya Sakai, Fujisawa; Nobuo Shimma, Chigasaki; Masao Tsukazaki, Fujisawa; Isao Umeda, Yokohama; Toshikazu Yamazaki, Kamakura, all of (JP)

(73) Assignee: Basilea Pharmaceutica AG, a Swiss Company, Basel (CH)

( * ) Notice: Subject to any disclaimer, the term of this patent is extended or adjusted under 35 U.S.C. 154(b) by 0 days.

(21) Appl. No.: 09/263,027

(22) Filed: Mar. 5, 1999

(30) Foreign Application Priority Data

| Mar. 6, 1998 | (EP) | 98104036 |
| Dec. 8, 1998 | (EP) | 98123310 |
| Jan. 26, 1999 | (EP) | 99101360 |

(51) Int. Cl.$^7$ ............ C07D 417/06; A61K 31/425
(52) U.S. Cl. ............ 514/365; 548/204; 548/205
(58) Field of Search ............ 548/205, 204; 514/365

(56) References Cited

U.S. PATENT DOCUMENTS

| 4,861,879 | 8/1989 | Heeres et al. |
| 5,900,486 | 5/1999 | Ichihara et al. |

FOREIGN PATENT DOCUMENTS

| 45364/97 | 2/1998 | (AU) |
| 0667 346 | 8/1995 | (EP) |
| 92/17474 A | 10/1992 | (WO) |

OTHER PUBLICATIONS

Tasaka et al., Chem. Pharm. Bull. 41(6) pp. 1035–1042 (1993).

*Primary Examiner*—Robert Gerstl
(74) *Attorney, Agent, or Firm*—George W. Johnston; Dennis P. Tramaloni

(57) ABSTRACT

Azole derivatives of the formula I

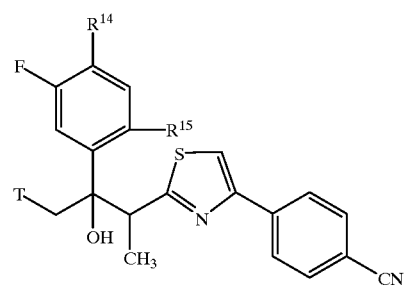

wherein
$R^{14}$, $R^{15}$ are each independently hydrogen or fluorine,
T is a group of the formula:

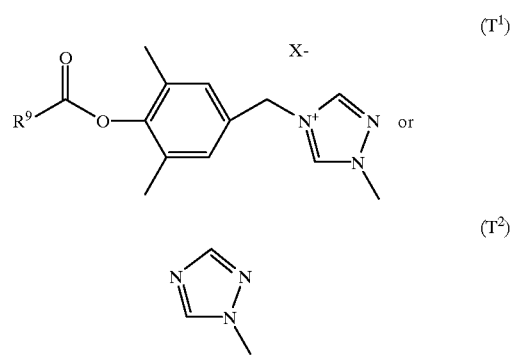

wherein
$R^9$ is pyrrolidinyl or a group A—NH—B—,
A is hydrogen or straight-chain or branched $C_1$–$C_5$ alkyl;
B is straight-chain or branched $C_1$–$C_4$ alkylene, —CH$_2$—CONH—CH$_2$ or —CH$_2$CH$_2$CH$_2$—CH(NH$_2$); and
$X^-$ is a pharmaceutically acceptable anion;
and pharmaceutically acceptable salts of said compounds, and hydrates and solvates of the compounds of formula I and the salts thereof can be used in the production of medicaments for treating fungal infections and mycoses.

37 Claims, No Drawings

AZOLES FOR TREATMENT OF FUNGAL INFECTIONS

The present invention relates to novel azoles of general formula I,

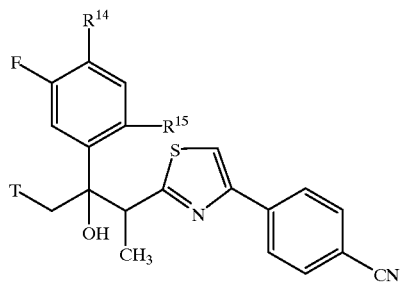

wherein:
$R^{14}$, $R^{15}$ are each independently hydrogen or fluorine,
T is a group of the formula:

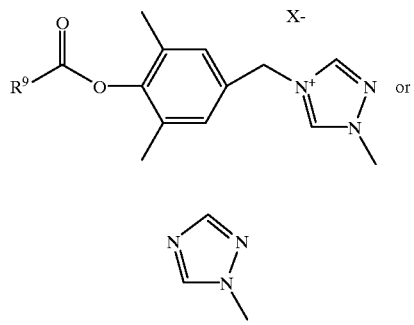

wherein
$R^9$ is pyrrolidinyl or a group A—NH—B—,
A is hydrogen or straight-chain or branched $C_1$–$C_5$ alkyl;
B is straight-chain or branched $C_1$–$C_4$ alkylene, —CH$_2$—CONH—CH$_2$ or —CH$_2$CH$_2$CH$_2$—CH(NH$_2$); and
$X^-$ is a pharmaceutically acceptable anion.
The present invention further relates to processes for the manufacture of said azoles, pharmaceutical compositions, particularly antifungal compositions, containing said azoles, and the use of these azoles for the production of medicaments for the treatment of fungal infections.

SUMMARY

Several azoles are currently used for systemic mycoses. However, none of them fully satisfies the requirements of the clinical setting, particularly with regard to: broad antifungal spectrum including aspergillus fumigatus; less drug-drug interaction; and appropriate plasma half-life for once a day treatment. Other clinical requirements which are not fulfilled by the azoles currently in use are: efficacy against major systemic mycoses including disseminated aspergillosis; safety; and oral or parenteral formulations. Particularly, the demand for a parenterally administered azoles is increasing for the treatment of serious systemic mycoses. Most of the azoles on the market, as well as under development are highly lipophilic molecules that make the parenteral formulation difficult.

The novel azoles of formula I have less metabolic interaction liability which is a clear clinical advantage. Those azoles of formula I, wherein T is a group $T^1$, are water soluble compounds useful for the treatment of systemic mycoses and suitable for both oral and particularly parenteral administration. Thus, the invention also relates to a method for the therapy of fungal infections and mycoses, which comprises administering to the infected organism an effective amount of the novel azole compounds.

DETAILED DESCRIPTION

The novel azoles of the present invention have the formula

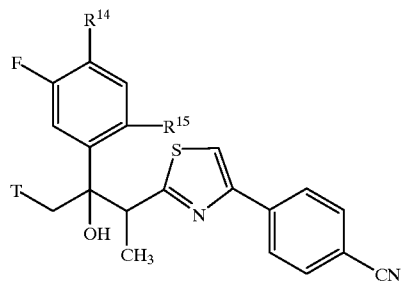

wherein $R^{14}$, $R^{15}$ are each independently hydrogen or fluorine,
T is a group of the formula:

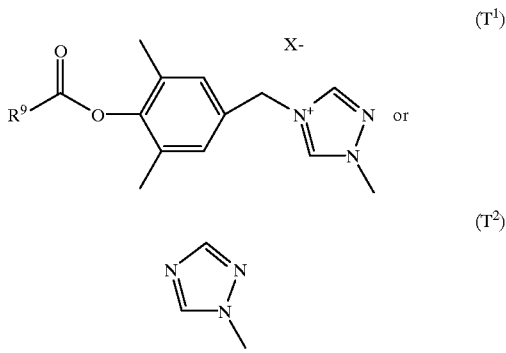

wherein
$R^9$ is pyrrolidinyl or a group A—NH—B—,
A is hydrogen or straight-chain or branched $C_1$–$C_5$ alkyl;
B is straight-chain or branched $C_1$–$C_4$ alkylene, —CH$_2$—CONH—CH$_2$ or —CH$_2$CH$_2$CH$_2$—CH(NH$_2$); and
$X^-$ is a pharmaceutically acceptable anion;

and pharmaceutically acceptable salts of said compounds, and hydrates and solvates of the compounds of formula I and the salts thereof.

Where T is $T^1$ in the above formula I, the azoles of the invention have the formula

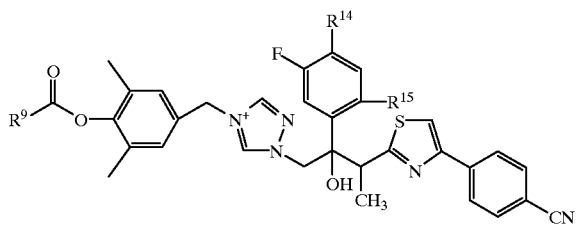

wherein
R⁹ is pyrrolidinyl or a group A—NH—B—,
A is hydrogen or straight-chain or branched $C_1$–$C_5$ alkyl;
B is straight-chain or branched $C_1$–$C_4$ alkylene, —$CH_2$—CONH—$CH_2$ or —$CH_2CH_2CH_2$—$CH(NH_2)$; and
$R^{14}$ and $R^{15}$ are each independently hydrogen or fluorine.
Where T is $T^2$ in the above formula I, the azoles of the invention have the formula

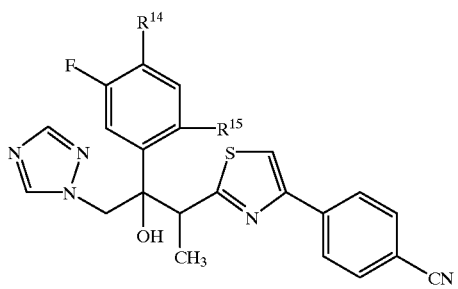

wherein $R^{14}$ and $R^{15}$ are each independently hydrogen or fluorine.

Preferred compounds of formula I (I' or II) are those wherein $R^{14}$ and $R^{15}$ are both H or F; or $R^{14}$ is H and $R^{15}$ is F.

Also preferred among the compounds of formula I' are those wherein R⁹ is 2-pyrrolidinyl, aminomethyl, (methylamino)methyl or (ethylamino)methyl.

The anion X⁻ can be derived from a pharmaceutically acceptable inorganic acid, and thus is a chloride, bromide, sulfate or the like. The anion X⁻ can also be derived from an organic acid, e.g. an aliphatic, aromatic or araliphatic carboxylic acid or sulfonic acid, and thus is an acetoxy, trifluoroacetoxy, mesyloxy or the like anion.

Examples of preferred azole compounds of the formula (I') are:

1-[(2R,3R)-3-[4-(4-cyanophenyl)-thiazol-2-yl]-2-(2,4,5-trifluorophenyl)-2-hydroxybutyl]-4-[(S)-3,5-dimethyl-4-(pyrrolidine-2-carbonyloxy)-benzyl]-1H-[1,2,4]triazol-4-ium bromide, and particularly its trifluoroacetic acid salt, 1-[(2R,3R)-3-[4-(4-cyanophenyl)-thiazol-2-yl]-2-(2,5-difluorophenyl)-2-hydroxybutyl]-4-[(S)-3,5-dimethyl-4-(pyrrolidine-2-carbonyloxy)-benzyl]-1H-[1,2,4]triazol-4-ium bromide, and particularly its trifluoroacetic acid salt, 1-[(2R,3R)-3-[4-{4-cyanophenyl)thiazol-2-yl)]-2-(3-fluorophenyl)-2-hydroxybutyl]-3-[(S)-3,5-dimethyl-4-(pyrrolidine-2-carbonyloxy)-benzyl]-1H-1,2,4-triazol-4-ium bromide, and particularly its trifluoroacetic acid salt, (2R,3R)-4-(4-aminoacetoxy-3,5-dimethylbenzyl)-1-[3-[4-(4-cyanophenyl)thiazol-2yl]-2-(2,4,5-trifluorophenyl)-2-hydroxynutyl]-1H-[1,2,4]triazol-4-ium bromide, and particularly its trifluoroacetic acid salt, (2R,3R)-4-(4-aminoacetoxy-3,5-dimethylbenzyl)-1-[3-[4-(4-cyanophenyl)thiazol-2-yl]-2-(2,5-difluorophenyl)-2-hydroxybutyl]-1H-[1,2,4]triazol-4-ium bromide, and particularly its trifluoroacetic acid salt, (2R,3R)-4-(4-aminoacetoxy-3,5-dimethylbenzyl)-1-[3-[4-(4-cyanophenyl)-thiazol-2-yl]-2-(3-fluorophenyl)-2-hydroxybutyl]-1H-[1,2,4]triazol-4-ium bromide, and particularly its trifluoroacetic acid salt, 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide, and particularly its trifluoroacetic acid salt, 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide, and particularly its trifluoroacetic acid salt, 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide, and particularly its trifluoroacetic acid salt, (2R,3R)-1-[3-[4-(4-cyanophenyl)thiazol-2-yl]-2-(2,4,5-trifluorophenyl)-2-hydroxybutyl]-4-[4-[(ethylamino)-acetoxy]-3,5-dimethylbenzyl]-1H-[1,2,4]triazol-4-ium bromide, and particularly its trifluoroacetic acid salt, (2R,3R)-1-[3-[4-(4-cyanophenyl)thiazol-2-yl]-2-(2,5-difluorophenyl)-2-hydroxybutyl]-4-[4-[(ethylamino)-acetoxy]-3,5-dimethylbenzyl]-1H-[1,2,4]triazol-4-ium bromide, and particularly its trifluoroacetic acid salt, 1-[(2R,3R)-3-[4-(4-cyanophenyl)thiazol-2-yl]-2-(3-fluorophenyl)-2-hydroxybutyl]-4-[3,5-dimethyl-4-[(ethylamino)acetoxy]benzyl]-1H-[1,2,4]triazol-4-ium bromide, and particularly its trifluroacetic acid salt, 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium chloride, and particularly its hydrochloric acid salt, 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1 ,2,4]triazol-4-ium chloride, and particularly its hydrochloric acid salt, 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium chloride, and particularly its hydrochloric acid salt, 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide hydrobromic acid salt, 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide hydrobromic acid salt, p0 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide hydrobromic acid salt, 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide hydrochloric acid salt, 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide hydrochloric acid salt, 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide hydrochloric acid salt.

Examples of preferred triazole compounds of the formula (II) are:

(2R,3R)-3-[4-(4-cyanophenyl)thiazol-2-yl)]-1-(1H-1,2,4-triazol-1-yl)-2-(2,4,5-trifluorophenyl)-butan-2-ol,
(2R,3R)-3-[4-(4-cyanophenyl)thiazol-2-yl)]-2-(2,5-difluorophenyl)-1-(1H-1,2,4-triazol-1-yl)-butan-2-ol,
(2R,3R)-3-[4-(4-cyanophenyl)thiazol-2-yl)]-2-(3-fluorophenyl)-1-(1H-1,2,4-triazol-1-yl)-butan-2-ol.

The following synthetic scheme 1 illustrates the manufacture of one of the compounds of formula I':

Synthetic scheme 1

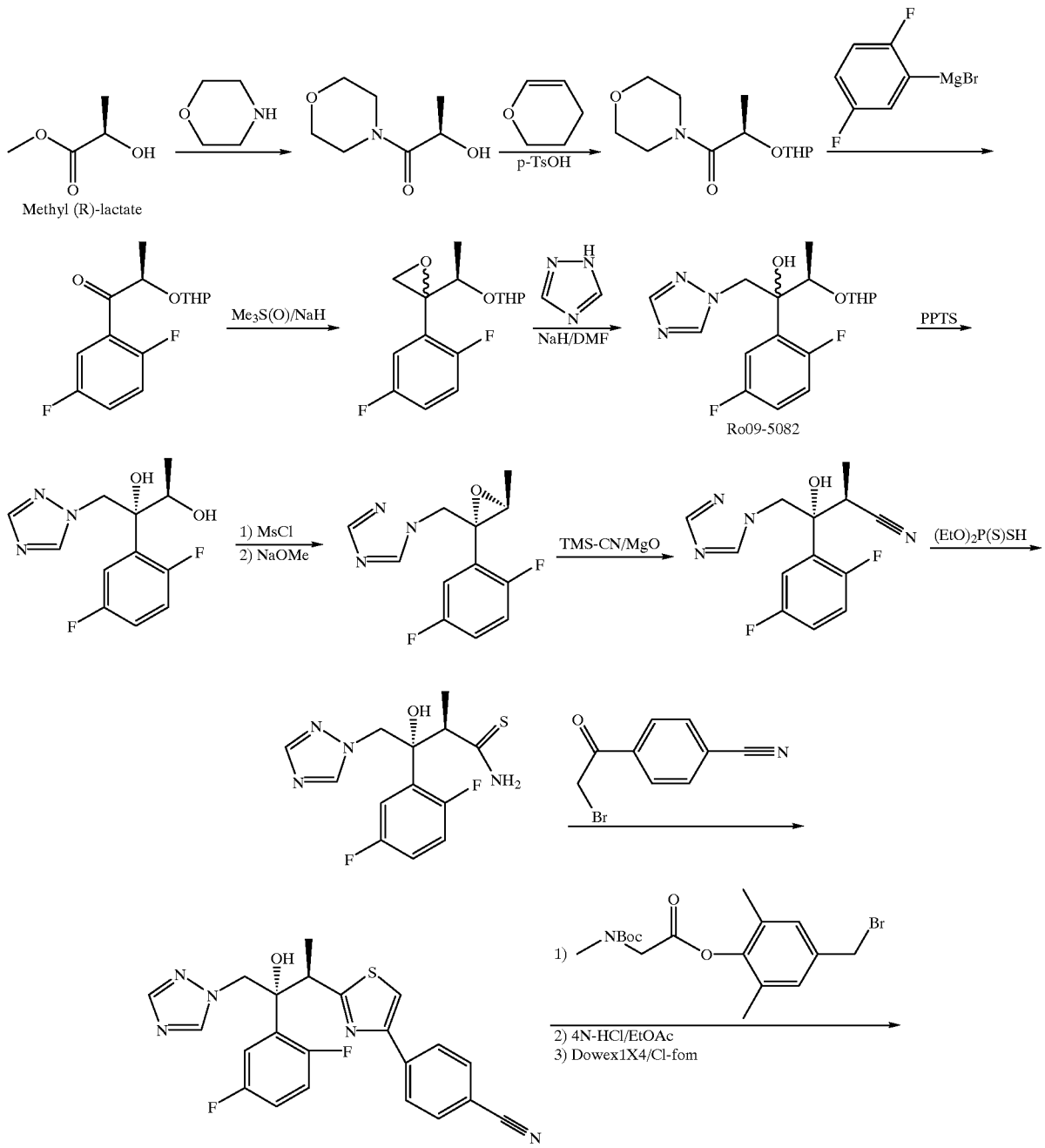

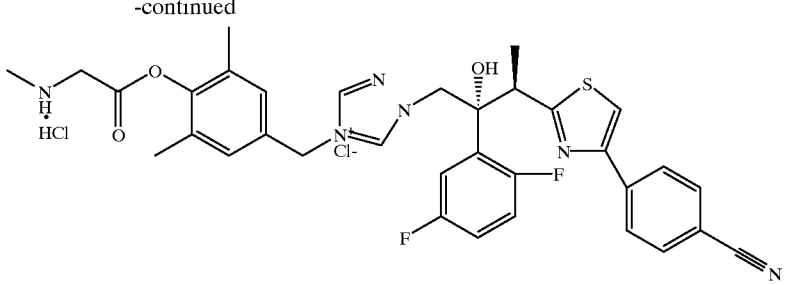

The novel azole compounds represented by the general formula I' as well as salts, hydrates or solvates thereof can be manufactured by reacting an azole compound of the above general formula (II) with a compound of the general formula (III), (III)

wherein:
R⁹ is pyrrolidinyl or a group A—NH—B—,
A is hydrogen or straight-chain or branched $C_1$–$C_5$ alkyl;
B is straight-chain or branched $C_1$–$C_4$ alkylene, —$CH_2$—$CONH$—$CH_2$ or —$CH_2CH_2CH_2$—$CH(NH_2)$ and,
an amino group present in R⁹ may be in protected form; and L is a leaving group, followed if necessary, by removal of a protecting group and/or by salt formation.

The benzylation reactions of the compound of the general formula (II) with the compound of the general formula (III) can be carried out in a solvent such as methylene chloride, chloroform, benzene, toluene, acetonitrile, tetrahydrofuran, dioxane, or dimethylformamide, preferably chloroform, acetonitrile, or dimethylformamide. The reaction time of this benzylation reaction may be varied within a relatively wide range. In general, the reaction can be carried out at a temperature between 0° C. and 100° C., preferably between 0° C. and 50° C. Preferably, an amino group present in R⁹ in the compound of formula III is protected by a suitable amino protecting group, such as tert.-butoxycarbonyl. The protecting group may, if necessary, be removed after the reaction by procedures known to those skilled in the art.

The compounds of formula (I') may contain an amino acid ester substituent R⁹ which substituents may form acid addition salts. The term "salts of compounds of formula (I')" in the present specification, refers to such acid addition salts. These salts may be derived from pharmaceutically acceptable acids as described earlier with reference to the symbol X⁻. The salt formation can be performed when removing a protecting group, or can be performed ad hoc by procedures known per se.

The hydration can be effected in the course of the manufacturing process or can occur gradually as a result of hygroscopic properties of an initially anhydrous product. Solvates with pharmaceutically acceptable solvents such as ethanol can be obtained for example, during crystallization.

The azoles of formula (II) as well as salts, hydrates or solvates thereof can be manufactured according to the following synthetic scheme 2, starting from 4-[(2R)-2-(3,4,5,6-tetrahydro-2H-pyran-2-yloxy)propionyl]morpholine [which can be prepared by a same procedure as described in Chem. Pharm. Bull. 41, 1035, 1993.].

Synthetic scheme 2

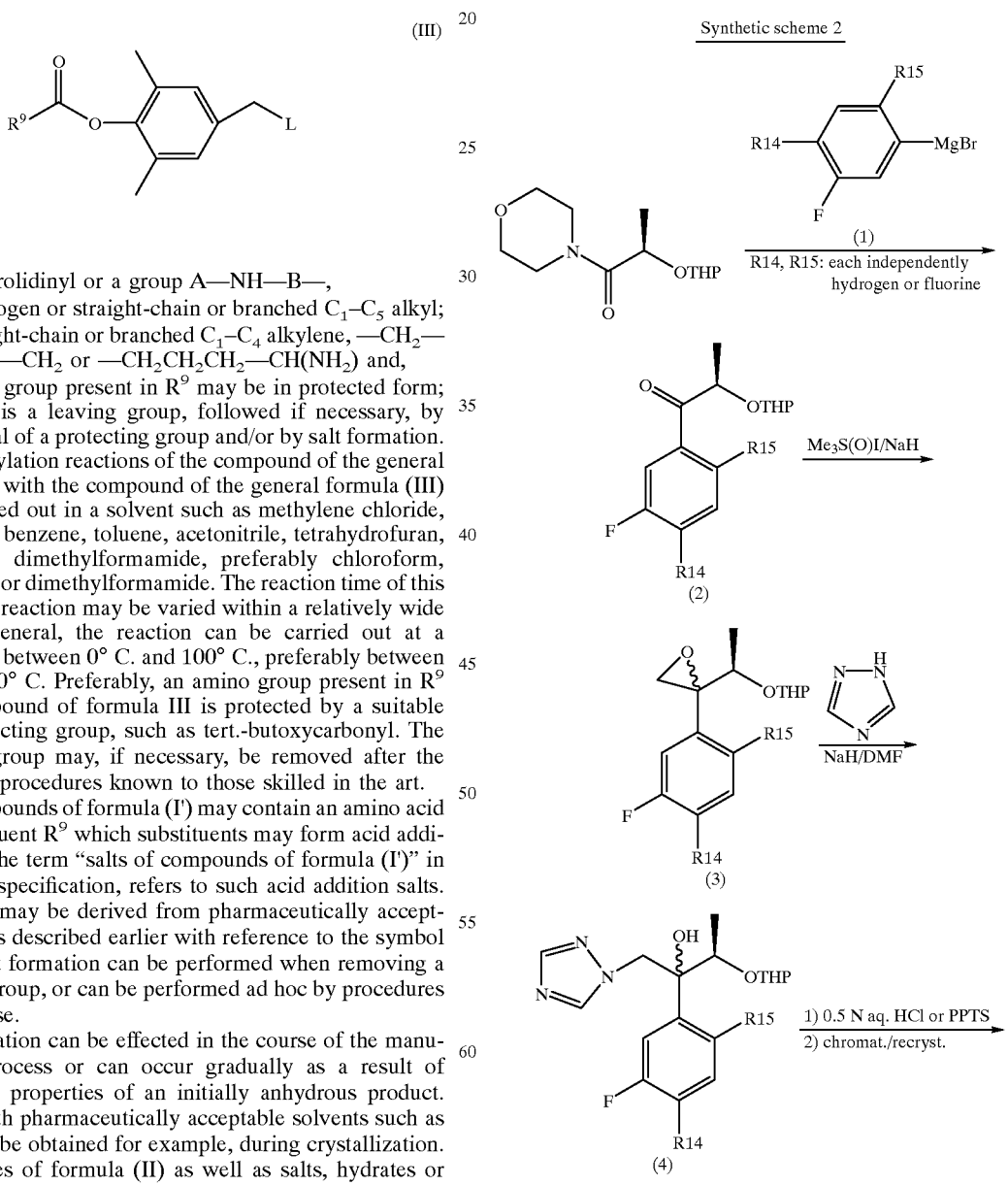

-continued

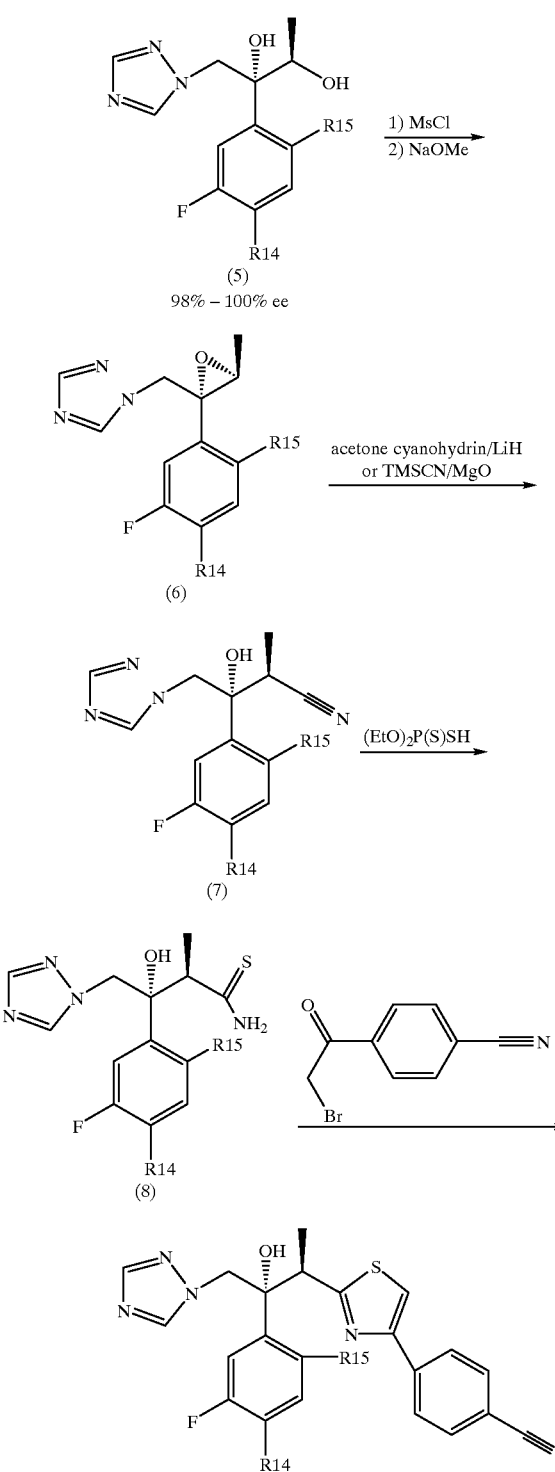

(a) Reacting 4-[(2R)-2-(3,4,5,6-tetrahydro-2H-pyran-2-yloxy)propionyl]morpholine with a compound of the formula (1) in an organic solvent such as tetrahydrofuran (THF) at a temperature between −10° C. and room temperature for 3 to 8 hr. to give a compound of the formula (2),

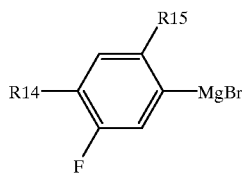

(1)

in which $R^{14}$ and $R^{15}$ are each independently hydrogen or fluorine atom (throughout this reaction scheme, $R^{14}$ and $R^{15}$ shall have this meaning), followed by (b) reacting a compound of the formula (2) with trimethyl sulfoxonium iodide, in the presence of sodium hydride in THF and dimethyl sulfoxide (DMSO) or in the presence of BuLi in THF and N,N'-dimethylpropylene urea (DMPU), at a temperature between −5° C. and room temperature for 2 to 8 hr. to give a compound of the formula (3),

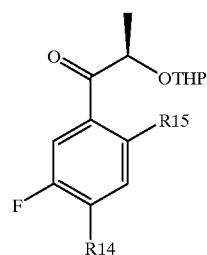

(2)

followed by (c) reacting a compound of the formula (3) with triazole in the presence of sodium hydride in dry dimethylformamide (DMF) at a temperature between 50° C. and 100° C. for 6 to 12 hr. to give a compound of the formula (4),

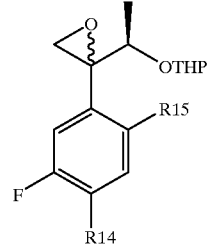

(3)

followed by (d) reacting a compound of the formula (4) with aqueous hydrochloric acid at a concentration between 1.0N and 0.1N solution, in methanol and n-hexane at room temperature or pyridinium p-toluenesulfonate in ethanol, at a temperature between room temperature and 100° C. for 2 to 6 hr. The resulting compound is recrystalized from t-butyl methyl ether and n-hexane to give a compound of the formula (5),

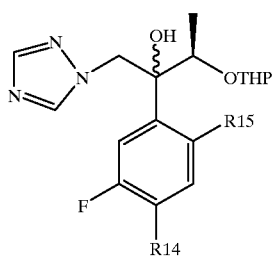

(4)

followed by (e) reacting a compound of the formula (5) with mesyl chloride in $CH_2Cl_2$ and methyl acetate (AcOEt) in the presence of an organic base such as triethylamine or pyridine for 30 min. to 2 hr. This reaction is followed by epoxy ring formation with sodium methoxide in methanol for 15 min. to 1 hr. The resulting compound is purified by recrystalization from t-butyl methyl ether and n-hexane or by silicagel column chromatography using $CH_2Cl_2$ and methanol as eluent, to give a compound of the formula (6),

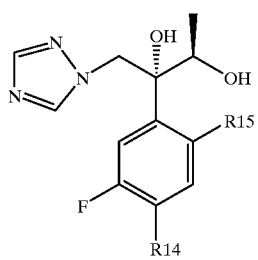

(5)

followed by (f) reacting a compound of the formula (6) with acetone cyanohydrin in the presence of lithium hydride in THF under reflux for 4 to 8 hr. or trimetylsilyl cyanide in the presence of magnesium oxide in o-xylene at a temperature between 100° C. and 160° C. for 20 to 40 hr, then removing of trimethylsilyl group with conc. hydrogen chloride solution in THF to give a compound of the formula (7),

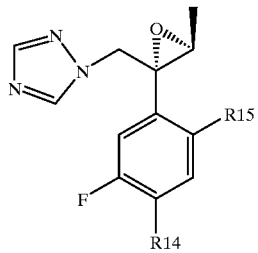

(6)

followed by (g) reacting a compound of the formula (7) with dithiophosphoric acid O,O-diethyl ester and water or dithiophosphoric acid O,O-diethyl ester, water and iso-propanol at a temperature between 90° C. and 150° C. for 4 to 8 hr. to give a compound of the formula (8),

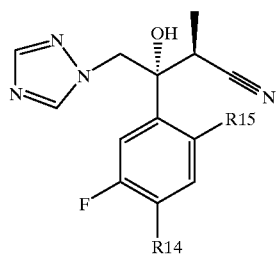

(7)

followed by (h) reacting a compound of the formula (8) with 2-bromo-4'-cyanoacetophenone at a temperature between room temperature and 80° C. in acetonitrile, ethanol or methanol for 2 to 24 hr. to give a compound of the formula (II),

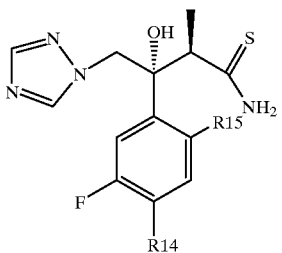

(8)

The azoles of formulae I' and II with a configuration other than 2R,3R can be synthetized in a way similar to that described above.

The term "salts of compounds of the formula (II)" in the present specification refers to acid addition salts. These salts may be derived from pharmaceutically acceptable acids such as acetic acid and hydrogen chloride.

The salt formation can be performed by procedures well known in the art Hydrates or solvates with pharmaceutically acceptable solvents such as ethanol can be obtained for example, during crystallization.

Fungal infections usually occur in immunocompromised patients with underlying diseases. Antifungal agents are, therefore, often taken with other medications. When co-administered with other drugs, azole antifungals have been reported to increase the blood concentrations of some of the drugs administered concomitantly. Such drug-drug interactions can sometimes result in severe adverse effects and sometimes form a basis for contraindication. This is one of critical issues of azole antifungals such as itraconazole, fluconazole and ketoconazole. The novel azoles represented by the formula (II) as well as hydrates or solvates thereof have less drug-drug interaction than known antimycotic azole compounds (see Table 1). Therefore, these azoles would have a clear clinical advantage.

In vitro P450 Inhibitory Activity

Each azole compound at different concentrations was incubated with a specific substrate for each CYP, human liver microsomes and NADPH at 37° C. Then, the metabolite formed from the specific substrate was determined by HPLC and the 50% inhibitory concentration ($IC_{50}$) was calculated. The substrate concentrations and incubation conditions were as follows:

(1) substrate for CYP3A4: midazolam (10 $\mu$M), formation of 1-hydroxymidazolam after incubation for 10 min at 37.
(2) substrate for CYP2C9: tolbutamide (100 $\mu$M), formation of 4-hydroxytolbutamide after incubation for 10 min at 37.

TABLE 1

In vitro inhibitory activity of azole antifungals against Cytochrome P450 isozymes using human liver microsomes

| | P450 inhibition IC50 ($\mu$M) | |
|---|---|---|
| | CYP 3A4(1) | CYP 2C9(2) |
| Ketoconazole | 0.19 | 13.9 |
| Itraconazole | 0.36 | 25.7 |
| Fluconazole | 50 | >50 |
| Example 5 | 23 | 18.4 |
| Example 4 | 4.1 | 35.1 |

In vitro Antifungal Activities

The in vitro antifungal activities were evaluated by determining the 80% inhibitory concentration ($IC_{80}$), which were calculated as the lowest concentration of an antifungal to inhibit the growth of fungus to 20% turbidity compared with the drug-free control growth spectrophotometrically.

The $IC_{80}$ values were determined by the broth microdilution procedure based on NCCLS Approved Standard [National Committee for Clinical Laboratory Standards (1997). Reference method for broth dilution antifungal susceptibility testing of yeasts. Approved standard. Document M27-A] with the following minor modification: RPMI1640 medium used for filamentous fungi was solidified with 0.2% low melting point agarose (BRL).

In vitro antifungal spectrum of the azole compounds of the present invention are shown in Table 2.

TABLE 2

Geometric mean of $IC_{80}$ of Azoles against reference strains

| | n= | Fluconazole | Itraconazole | Example 4 |
|---|---|---|---|---|
| C. albicans | 3 | 0.87 (0.31–6) | 0.008 (0.059) | 0.014 (0.0054–0.082) |
| C. glabrata | 2 | 5.2 (5–5.4) | 0.078 (0.041–0.059) | 0.090 (0.051–0.16) |
| C. guillier-mondii | 2 | 2.3 (1.9–2.9) | 0.032 (0.022–0.047) | 0.071 (0.053–0.094) |
| C. tropicalis | 2 | 0.59 (0.25–1.4) | 0.35 (0.0054–23) | 0.33 (0.019–2.7) |
| C. krusei | 2 | 25 (19–33) | 0.038 (0.023–0.064) | 0.11 (0.069–0.19) |
| C. parapsilosis | 2 | 1.6 (1.0–2.5) | 0.017 (0.017) | 0.025 (0.02–0.32) |
| C. lusitaniae | 2 | 0.18 (0.1–0.32) | 0.0021 (0.0014–0.0031) | 0.0051 (0.0027–0.0095) |
| C. neoformans | 2 | 3.7 (3.1–4.3) | 0.015 (0.012–0.018) | 0.042 (0.042–0.068) |
| A. fumigatus | 10 | >88 (45->100) | 0.027 (0.012–0.086) | 0.11 (0.060–0.28) |
| F. solani | 6 | >100 (>100) | 47 (17->100) | 11 (4.0–2.3) |
| F. moniliforme | 2 | >100 (>100) | 4.3 (0.021–0.69) | 1.8 (1.2–2.8) |
| A. corymbifera | 5 | >100 (>100) | 0.053 (0.021–0.078) | 0.37 (0.18–1.3) |
| R. pusillus | 3 | >90 (90->100) | 0.19 (0.012–33) | 0.68 (0.24–3.1) |
| R. oryzae | 4 | >100 (>100) | 0.18 (0.045–2.2) | 0.59 (0.18–2.9) |
| R. microsporus | 3 | >100 (>100) | 0.29 (0.19–0.33) | 1.1 (0.59–0.69) |
| C. bertholletiae | 2 | >100 (>100) | 0.22 (0.15–0.33) | 5.9 (5.9) |

Therefore, the triazole compounds of the formula (II) as well as salts, hydrates or solvates thereof, according to the present invention, exhibit potent antifungal activity against various fungal infections including Aspergillosis in mice over a very wide range of dosages both orally and parenterally and are useful as antifungal agents.

The novel azole compounds represented by the general formula (I') as well as hydrates or solvates thereof have high water solubility particularly in comparison to known antimycotic azole compounds. The solubility of two products of the invention is given in Table 3.

TABLE 3

| Compound (Example No.) | solubility in distilled water (mg/ml) |
|---|---|
| 1 | 22 |
| 3 | >7 |

In addition, the azole of formula I' are chemically stable in aqueous solution at room temperature more than three days, but are efficiently converted into compounds of formula (II) in either mouse, rat, monkey or human plasma. The conversion of representatives of the new azole compounds of the general formula (I') to compounds of formula (II) in human plasma are shown in Table 4. The compounds of formula (I') were incubated with human plasma at a concentration of 10 $\mu$g/ml at 37° C. for up to 20 min.

TABLE 4

Conversion of compounds of formula (I') to compounds of formula (II) in human plasma

| Example No. | Conversion half-life (min) | Incubation time (min) | Observed (%) Comp. (I') | Compound(II) |
|---|---|---|---|---|
| 1 | <1 | 5 | <5 | 96 |
| 3 | <1 | 5 | <5 | 89 |

In vivo efficacy of the compounds of the present invention is shown in Table 5. Male Fisher rats, strain F344/DuCrj, were employed for experimental infection models such as systemic candidiasis, systemic aspergillosis and pulmonary aspergillosis model. Immunocompetent 4 weeks old rats were used for systemic candidiasis or systemic aspergillosis which occurred after infection with Candida albicans conidia of $5 \times 10^6$/rat or with Aspergillus fumigatus conidia of $6 \times 10^5$/rat via tail vein. Otherwise, for pulmonary aspergillosis model, rats had been immunosuppressed by cortisone acetate treatments prior to infection with $2 \times 10^5$/rat intratrachially. Treatments were given twice on the first day, and once daily on the following 4 days, both for systemic and pulmonary aspergillosis. For systemic candidiasis rats were treated at 0, 4, 24, and 48 h after infection. Effective dose 50% ($ED^{50}$) values were determined on day 14 after infection.

TABLE 5

($\mu$mol/kg)

| | Systemic candidiasis | | Pulmonay aspergillosis | | Systemic aspergillosis | |
|---|---|---|---|---|---|---|
| | iv. | p.o. | p.o. | i.v. | p.o. | i.v. |
| Example 1 | 5.3 | 5.3 | 7.4 ± 3.8 | 8.0 ± 4.2 | 5.8 | 3.0 |
| Itraconazole | n.t. | 3.9 ± 2.2 | n.t. | 2.0 ± 1.1 | n.t. | 4.0 |
| Fluconazole | n.t. | 1.4 | n.t | n.t. | n.t. | n.t. |

Therefore, the water soluble compounds of the general formula (I') as well as the salts, hydrates or solvates thereof exhibit potent activity against various fungal infections including Aspergillosis in rats over a very wide range of dosages both orally and parenterally and are useful as antifungal agents.

The present invention further relates to the pharmaceutical compositions containing an azole compound of the general formula I or a salt, hydrate or solvate thereof.

The azole compounds of the formula I as well as salts, hydrates or solvates thereof are very active antimycotic agents. They are active against a variety of fungal species including Candida spp., *Cryptotoccus neoformans*, Aspergillus spp., Trichophyton spp., Microsporum spp., Exophiala spp., *Blastomyces dermatitidis,* and *Histoplasma capsulatum.* Thus, the compounds of the present invention are useful for topical and systemic treatment of mycoses in animals as well as in humans. For example, they are useful in treating topical and mucosal fungal infections caused by, among other genera, Candida, Trichophyton, or Microsporum. They may also be used in the treatment of systemic fungal infections caused by, for example, Candida spp., *Cryptococcus neoformans,* Aspergillus spp., Paracoccidiodes spp., Sporotrix spp., Exophiala spp., Blastomyces spp., or Histoplasma spp.

For clinical use, the azole compound of the formula I as well as salts, hydrates or solvates thereof can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration. Pharmaceutical formulation for oral administration may be granule, tablet, sugar coated tablet, capsule, pill, suspension or emulsion. For parenteral injection, for example, intravenously, intramuscularly or subcutaneously, the azoles of formula I may be used in the form of a sterile aqueous solution or in the form of a HPCD complex, which may contain other substances, for example, salts or glucose to make the solution isotonic. The azoles can also be administered in the form of a suppository or pessary, or they may be applied topically in the form of a lotion, solution, cream, ointment or dusting powder.

The daily dosage level of the azole compounds of the formula I is from about 0.1 to about 50 mg/kg (in divided doses) when administered in one, two or more dosages by either the oral or parenteral route. Thus, tablets or capsules may contain from about 5 mg to about 0.5 g of active compound for administration. In any event the actual dosage can be determined by the physician and it may be varied upon the age, weight and response of the particular patient.

In addition, the azole compounds of the formula I as well as salts, hydrates or solvates thereof have activity against a variety of plant pathogenic fungi, including for example *Pyricularia oryzae, Pythium aphanidermatum,* Alternaria spp., and *Paecilomyces variotii.* Thus, they can be applied for agricultural and horticultural purposes preferably in the form of a composition formulated as appropriate to the particular use and purpose desired, for example dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compounds having herbicidal or insecticidal, or additional antiflugals can be incorporated in the compositions. The compounds and compositions can be applied in a number of ways, for example they can be applied directly to the plant foliage, stems, branches, seeds or roots or to the soil or other growing medium, and they may be used not only to eradicate the disease, but also prophylactically to protect the plants or seeds from attack.

The following examples merely illustrate the preferred methods for the preparation of the compounds of the present invention and are not intended to limit the scope of the invention thereto.

EXAMPLE 1 a) Preparation of (2R)-2',5'-Difluoro-2-(3,4,5,6-tetrahydro-2H-pyran-2-yloxy)-propiophenone A mixture of magnesium (7.25 g, 0.298 mol) and iodine (catalytic amount) and 1-bromo-2,5-difluorobenzene (20.0 g, 0.178 mol) in THF (250ml) was vigously stirred. The color of iodine was disappeared and the inner temperature rose up to 65° C. To this mixture was added additional 1-bromo-2,5-difluorobenzene (30.0 g, 0.267 mol) dropwise to maintain the inner temperature from 50 to 55° C. over 45min. The resulting mixture was stirred at 55° C. for 30min. then at r.t. for 1 hr. The mixture was cooled down to −5° C. To this mixture was added a solution of 4-[(2R)-2-(3,4,5,6-Tetrahydro-2H-pyran-2-yloxy)propionyl] morpholine (52.5 g, 0.216 mol) in THF (150ml) dropwise over 40min. And the resulting mixture was stirred at r.t. for 4hrs. The reaction mixture was cooled down to 5° C. and saturated $NH_4Cl$ aq. (100ml) was added carefully. The whole was diluted with $H_2O$ (600ml) and extracted with EtOAc (400 ml+200 ml×2). The combined organic layer was dried over $Na_2SO_4$ and concentrated in vacuo. The residue was chromatographed on silica gel (n-hexane: EtOAc=10:1~5:1) to give (2R)-2',5'-Difluoro-2-(3,4,5,6-tetrahydro-2H-pyran-2-yloxy)-propiophenone (47.3 g, 81%) as pale yellow syrup.

Physical form: colorless oil; FAB-MS: m/z 271$(M+H)^+$; $^1$H-NMR(CDCl$_3$): 1.42~1.90(9H,m),3.32~3.40(1H×½,m), 3.69~3.77(1H×½,m), 3.86~3.94 (1H×½,m),4.66(1H×½,t,J=3.6Hz),4.75(1H'½, t,J=3.6Hz), 4.87(1H×½,q,J=6.6Hz), 5.11 (1H×½,q,J=6.9Hz),7.08~7.25(2H,m),7.49~7.55(1H,m).

b) Preparation of 2-(2,5-Difluorophenyl)-2-[(1R)-1-(3,4,5,6,-tetrahydro-2H-pyran-2-yloxy)ethyl]oxirane To a stirred mixture of NaH (60% in oil, 9.1 g, 0.228 mol) in DMSO (300ml) was added portionwise trimethylsulfoxonium iodide (53.9 g, 0.245 mol) at the inner temperature with the range from 15° C. to 18° C. over 20 min. The ice bath was removed and the mixture was stirred at r.t. for 3 hrs. The mixture was cooled down to 10° C. To this mixture was added a solution of (2R)-2',5'-Difluoro-2-(3,4,5,6-tetrahydro-2H-pyran-2-yloxy)-propiophenone (47.3 g, 0.175 mol) in DMSO (150 ml) dropwise over 20 min. The resulting mixture was stirred at r.t. for 4 hrs. The reaction mixture was poured into ice-water (800 ml). The whole was extracted with EtOAc (400 ml+200 ml×2). The combined organic layer was washed with brine, dried over $Na_2SO_4$ and concentrated in vacuo. The residue was chromatograkkphed on silicagel (n-hexane: EtOAc=8:1~5:1) to give 2-(2,5-Difluorophenyl)-2-[(1R)-1-(3,4,5,6,-tetrahydro-2H-pyran-2-yloxy)ethyl]oxirane (48.3 g, 97% ).

Physical form: pale yellow syrup, EI-MS: m/z 284 $(M)^+$; $^1$H-NMR(CDCl$_3$): 1.15(3H×½,dd,J=6.6,1.3Hz), 1.24(3H× ½,dd, J=6.6,1.3Hz), 1.52~1.87(6H,m),2.83~2,90(1H,m), 3.07 (1H×½,d,J=5.3Hz),3.36(1H×½,d,J=5.6Hz), 3.48~3.56

(1H,m),3.82~3.92 (1H,m),4.00~4.16(1H,m),4.73~4.92(1H, m), 6.96~7.02(1H,m),7.09~7.15 (1H,m).

c) Preparation of (3R)-2-(2,5-difluorophenyl)-3-(3, 4,5,6-tetrahydro-2H-pyran-2-yloxy)-1-(1H-1,2,4-triazol-1-yl)-2-butanol To a stirred suspension of NaH (60% in oil, 21.0 g, 0.525 mol) in DMF (300 ml) was added portionwise 1,2,4-triazole (43.3 g, 0.627 mol) at the inner temperature from 2° C. to 11° C. over 30 min. The resulting mixture was stirred at r.t. for 1.5 hrs. To this mixture was added a solution of 2-(2,5-Difluorophenyl)-2-[(1R)-1-(3,4,5,6-tetrahydro-2H-pyran-2-yloxy)ethyl]oxirane (48.3 g, 0.170 mol) in DMF (50 ml). The mixture was stirred at 60° C. for 1 hr. and then at 65° C. for 14 hrs. The reaction mixture was cooled down to 10° C. and then poured into ice-water (800 mL ). The resulting mixture was extracted with EtOAc (400 ml+200 ml×2 ). The combined organic layer was dried over $Na_2SO_4$ and concentrated in vacuo. The residue was chromatographed on silicagel (n-hexane: EtOAc=4:1~1:5) to give (3R)-2-(2, 5difluorophenyl)-3-(3,4,5,6-tetrahydro-2H-pyran-2-yloxy)-1-(1H-1,2,4-triazol-1-yl)-2-butanol (43.9 g, 73% ) and recovered starting material (13.2 g, 27%). Physical form: colorless syrup; FAB-MS: m/z 354 (M+H)$^+$; $^1$H-NMR (CDCl$_3$): 1.00(3H×½,d,J=6.6Hz),1.13(3H×½,d,J=6.6Hz), 1.42~1.88(6H,m)3.38~3.60(1H,m),3.80~4.00(1H,m), 4.32~5.02(5H,m),6.83~6.99 (2H,m),7.14~7.21(1H,m),7.73 (1H×½,s),7.74(1H×½,s),7.92(1H×½,s)7.95(1H×½,s), d) Preparation of (2R,3R)-2-(2,5-difluorophenyl)-1-(1H-1,2,4-triazol-1-yl)-2,3-butanediol A mixture of (3R)-2-(2,5-difluorophenyl)-3-(3,4,5,6-tetrahydro-2H-pyran-2-yloxy)-1-(1H-1,2,4-triazol-1-yl)-2-butanol (43.9 g, 0.124 mol) and PPTS (15.6 g, 62.1 mmol) in EtOH ( 400 ml ) was stirred at 55° C. for 5 hrs. The mixture was was evaporated to remove solvent down to 100 ml. The residue was poured into ice-aqueous NaHCO$_3$ (500 ml). The whole was extracted with EtOAc (400 ml+200 ml×2). The combined organic layer was dried over $Na_2SO_4$ and concentrated in vacuo. The residue was chromatographed on silicagel (CH$_2$Cl$_2$: MeOH=20:1) to give (2R, 3R)-2-(2,5-difluorophenyl)-1-(1H-1,2,4-triazol-1-yl)-2,3-butanediol (18.0 g, 54%).

Physical form: colorless syrup; FAB-MS: m/z 270 (M+H)$^+$; $^1$H-NMR(CDCl$_3$): 0.99(3H,d,J=6.6 Hz),2.61(1H, d,J=10.6 Hz), 4.31~4.36 (1H,m),4.79,4.88 (2H,ABq,J=14.5 Hz),4.84(1H,s),6.84~6.99(2H,m),7.13~7.19(1H,m),7.84 (1H,s),7.85(1H,s).

e) Preparation of (2R,3S)-2-(2,5-Difluorophenyl)-3-methyl-2-[(1H-1,2,4-triazol-1-yl)-methyl]-oxirane To a cold (0° C.) and stirred solution of (2R,3R)-2-(2,5-difluorophenyl)-1-(1H-1,2,4-triazol-1-yl)-2,3-butanediol (35.0 g, 0.130 mol) and triethylamine (54.8 ml, 0.393 mol) in CH$_2$Cl$_2$ (500 ml) was added a mesylchloride (12.1 ml, 0.156 mol) dropwise over 5 min. The resulting mixture was stirred at r.t. for 1.5 hrs. The reaction mixture was poured into ice-water (300 ml). The resulting mixture was shaken well and the organic layer was separated. The aqueous layer was further extracted with CH$_2$Cl$_2$ (150 ml×2). All the organic layers were combined, dried over $Na_2SO_4$ and concentrated in vacuo to give mesylate (46.7 g) as crude syrup. The obtained mesylate was dissolved in MeOH (500 ml) and the solution was cooled down to 0° C. To this solution was added 28% NaOMe methanol solution (29.0 ml). The mixture was stirred at 0° C. for 50 min. The reaction mixture was evaporated to reduce the volume of the solvent down to 150 ml. The residue was poured into ice-water (300 ml). The resulting mixture was extracted with ethylacetate (300 ml+200 ml×2). The combined organic layer was dried over $Na_2SO_4$ and concentrated in vacuo. The residue was cromatographed on silicagel (hexane: EtOAc= 1:3) to give (2R,3S)-2-(2,5-Difluorophenyl)-3-methyl-2-[(1H-1,2,4-triazol-1-yl)-methyl]-oxirane (30.3 g, 93%).

Physical form: white solid; FAB-MS: m/z 252 (M+H)$^+$; $^1$H-NMR(CDCl$_3$): 1.64(3H,d,J=5.6 Hz),3.19(1H,q,J=5.6 Hz),4.42,4.97 (2H,ABq,J=14.8 Hz), 6.75~6.81(1H,m), 6.89~7.01(2H,m),7.83(1H,s),7.98 (1H,s).

f) Preparation of (2S,3R)-3-(2,5-Difluoro-phenyl)-3-hydroxy-2-methyl-4-[1,2,4]triazol-1-yl-butyronitrile A mixture of (2R,3S)-2-(2,5-Difluorophenyl)-3-methyl-2-[(1H-1,2,4-triazol-1-yl)-methyl]-oxirane (30.3 g, 0.121 mol), trimethylsilylcyanide (65.0 ml) and MgO (24.5 g) in o-xylene (400 ml) was stirred at 130° C. for 10 hrs. To this mixture was added additional trimethylsilylcyanide (20.0 ml) and MgO (8.5 g) and the resulting mixture was stirred at 130° C. further for 6 hrs. The reaction mixture was cooled down to r.t. The precipitate was filtered off and washed with CH$_2$Cl$_2$. The filtrate was concentrated in vacuo to give crude brown syrup.

This crude syrup was dissolved in THF (600 ml) and the solution was cooled down to 0° C. To this mixture was added 1.0 M tetra n-butylammoniumfluoride THF solution (133 ml, 0.133 mol) dropwise over 5 min. The mixture was stirred at r.t. for 50 min. The solvent was removed under reduced pressure down to 150 ml. The residue was poured into ice-water (400 ml). The resulting mixture was extracted with EtOAc (300 ml+200 ml×2). The combined organic layer was dried over $Na_2SO_4$ and concentrated in vacuo. The residue was chromatographed on silicagel (n-hexane: EtOAc=1:3) to give (2S,3R)-3-(2,5-Difluoro-phenyl)-3-hydroxy-2-methyl-4-[1,2,4]triazol-1-yl-butyronitrile (30.5 g, 91%).

Physical form: colorless syrup; FAB-MS: m/z 279 (M+H)$^+$; $^1$H-NMR(CDCl$_3$): 1.19(3H,d,J=7.3 Hz),3.33(1H, q,J=7.3 Hz),4.82,5.00 (2H,ABq,J=13.9 Hz), 5.56(1H,brs), 6.89~7.04(2H,m),7.12~7.19(1 H,m),7.85(1 H,s),7.86(1H,s).

g) Preparation of (2R,3R)-3-(2,5-Difluoro-phenyl)-3-hydroxy-2-methyl-4-[1,2,4]triazol-1-ylthiobutyramide A mixture of (2S,3R)-3-(2,5-Difluoro-phenyl)-3-hydroxy-2-methyl-4-[1,2,4]triazol-1-yl-butyronitrile (30.5 g, 0.110 mol), diethyldithiophospate (235 ml) and H$_2$O (110 ml) was stirred at 80° C. for 2 hrs. The reaction mixture was cooled down to r.t. n-Hexane (400 ml) and water (200 ml) was added. The whole was shaken well and the aqueous layer was separated. The remaining organic layer was further extracted with H$_2$O (100 ml×3). All the aqueous layer was combined. Cooled down to 0° C. and neutralized and basified (PH8) with NaHCO$_3$. This basic(PH8) aqueous layer was extracted with EtOAc (300 ml+100 ml×3). The combined organic layer was dried over $Na_2SO_4$ and concentrated in vacuo to give dark brown syrup. By addition of CH$_2$Cl$_2$ (100 ml) to this crude syrup, precipitate was formed. The precipitate was filtered and washed with CH$_2$Cl$_2$-hexane (5:1 mixture) to give (2R,3R)-3-(2,5-Difluoro-phenyl)-3-hydroxy-2-methyl-4-[1,2,4]triazol-1-ylthiobutyramide (19.2 g, 56%) as white powder. On the other hand, the filtrate was concentrated in vacuo and the residue was chromatographed on silica gel (Wako-gel C-300, CH$_2$Cl$_2$:MeOH=20:1) to give additional (2R,3R)-3-(2,5-Difluoro-phenyl)-3-hydroxy-2-methyl-4-[1,2,4]triazol-1-ylthiobutyramide (7.46 g, 22%) as pale brown amorphous powder. Physical form: White solid; FAB-MS: m/z 313 (M+H)$^+$; $^1$H-NMR (CDCl$_3$): 1.12(3H,d,J=7.3 Hz),3.74(1H, q,J=7.3 Hz), 4.55,5.12 (2H,ABq,J=14.5 Hz), 5.84(1H,s), 6.85~7.02(2H,m),7.15~7.22(1H,m),7.80 (1H,s),7.89(1H,s), 7.89(1H,brs),8.43(1H,brs).

h) Preparation of 4-{2-[(1R,2R)-2-(2,5-Difluoro-phenyl)-2-hydroxy-1-methyl-3-[1,2,4]triazol-1-yl-propyl]-thiazol-4-yl}-benzonitrile A mixture of (2R,3R)-3-(2,5-Difluoro-phenyl)-3-hydroxy-2-methyl-4-[1,2,4]triazol-1-ylthiobutyramide (26.7 g, 85.4 mmol) and a-bromo-4'-cyano-acetophenone (24.0 g, 0.107 mol) in EtOH (500 ml) was refluxed for 1 hr. The reaction mixture was cooled down to r.t. And the solvent was removed under reduced pressure down to 150 ml. The residue was poured into in to cold (0° C.) saturated NaHCO$_3$ aq. (400 ml). The resulting mixture was extracted with EtOAc (300 ml+150 ml×2). The combined organic layer was washed with brine (200 ml), dried over Na$_2$SO$_4$ and concentrated in vacuo. The residue was chromatographed on silica gel (Wako-gel C-300, Hexane:EtOAc=1:2) to give 4-{2-[(1R,2R)-2-(2,5-Difluoro-phenyl)-2-hydroxy-1-methyl-3-[1,2,4]triazol-1-yl-propyl]-thiazol-4-yl}-benzonitrile (32.0 g, 86%).

Physical form: colorless heavy syrup; ESI-MS: m/z 437 (M)$^+$; $^1$H-NMR(CDCl$_3$): 1.25(3H,d,J=7.3 Hz),4.12(1 H,q, J=7.3 Hz),4.26,4.96 (2H,Abq,J=14.5 Hz), 5.75(1H,s), 6.89~7.07(2H,m),7.23~7.29(1 H,m),7.65 (1H,s),7.71(1H,s), 7.75, 8.02(4H,Abq,J=8.6 Hz),7.85(1H,s).

i) Preparation of 4-{4-[(tert-Butoxycarbonyl-methyl-amino)-acetoxy]-3,5-dimethyl-benzyl}-1-[(2R,3R)-3-[4-(4-cyano-phenyl)-thiazol-2-yl]-2-(2,5-difluoro -phenyl)-2-hydroxy-butyl]-1H-[1,2,4] triazol-4-ium bromide A mixture of 22.7 mg of 4-{2-[(1R,2R)-2-(2,5-Difluoro-phenyl)-2-hydroxy-1-methyl -3-[1,2,4]triazol-1-yl-propyl]-thiazol-4-yl}-benzonitrile and 25.0 mg of 4-tert-butoxycarbonyl-methyl-aminoacetoxy-3,5-dimethyl-benzyl bromide in CH$_3$CN(1.5 mL) was refluxed over 15 hrs. The solvent was evaporated in vacuo and the residue was chromatographed on silica gel (Wakogel C-200, solvent:CH$_2$Cl$_2$/MeOH=10/1) to give 4-{4-[(tert-Butoxycarbonyl-methyl-amino)-acetoxy]-3,5 -dimethyl-benzyl)}-1-[(2R,3R)-3-[4-(4-cyano-phenyl)-thiazol-2-yl]-2-(2,5-difluoro-phenyl)-2-hydroxy-butyl]-1H-[1,2,4]triazol-4-ium bromide (36.0 mg, 84% as colorless heavy syrup);

FAB-MS: m/z 743(M—Br)$^+$; $^1$H-NMR(CDCl$_3$): 1.23(3H, d,J=7.3 Hz), 1.47(9H,s),2.14(6H,s),3.03(3H,s),4.15(1H,q,J= 7.3 Hz),4.25(2H,s), 4.98,5.16(2H,ABq,J=13.9 Hz), 5.39~5.54(2H,m),6.27(1H,s),6.89~7.07(4H,m), 7.24~7.2 7(1H,m),7.58(1H,s),7.73,8.06(4H,ABq,J=8.58),8.07(1H,s), 11.26 (1H,s).

j) Preparation of 1-{(2R,3R)-3-[4-(4-cyano-phenyl)-thiazol-2-yl]-2-(2,5-difluoro-phenyl)-2-hydroxy-butyl}-4-(3,5-dimethyl-4-methylaminoacetoxy-benzyl)-1H-[1,2,4]triazol-4-ium bromide To a solution of 36 mg of 4-{4-[(tert-Butoxycarbonyl-methyl-amino)-acetoxy]-3,5-dimethyl-benzyl}-1-[(2R,3R)-3-[4-(4-cyano-phenyl)-thiazol-2-yl]-2-(2,5difluoro-phenyl)-2-hydroxy-butyl]-1H-[1,2,4]triazol-4-ium bromide in ethylacetate(2 ml) was added dropwise 4N HCl ethylacetate solution(1 mL) and the mixture was stirred at r.t. for 4 hrs. The precipitate was filtered and washed with diethylether to give 1-{(2R,3R) -3-[4-(4-cyano-phenyl)-thiazol-2-yl]-2-(2, 5-difluoro-phenyl)-2-hydroxy-butyl}-4-(3,5-dimethyl-4-methylaminoacetoxy-benzyl)-1H-[1,2,4]triazol-4-ium bromide (24.5 mg, 74% as HCl salt and as white solid);

FAB-MS: m/z 643 (M—Br)$^+$; $^1$H-NMR(DMSO-d): 1.19 (3H,d,J=7.3 Hz), 2.11(6H,s),2.64(3H,s),4.15(1H,q,J=7.3 Hz),4.41(2H,s),4.74,5.04(2H, ABq,J=14.5 Hz), 5. 40(2H,s), 6.76(1H,brs),7.10(2H,s),7.20~7.38(2H,m), 7.94,8.21(4H, ABq,J=8.25),8.45(1H,s),9.07(1 H,s),9.50(1H,brs),10.17 (1H,s).

EXAMPLE 2

Preparation of 1-[(2R,3R)-3-[4-(4-Cyanophenyl) thiazol-2-yl]-2-hydroxy-2-(2,5-difluorophenyl) butyl]-4-(3,5-dimethyl-4-methylaminoacetoxy-benzyl)-1H-[1,2,4]triazol-4-ium chloride hydrochloride 22.6 g of 1-{(2R,3R)-3-[4-(4-cyano-phenyl)-thiazol-2-yl]-2-(2,5-difluoro-phenyl)-2-hydroxy-butyl}-4-(3,5-dimethyl-4-methylaminoacetoxy-benzyl)-1H-[1,2,4]triazol-4-ium bromide was dissolved in 2 L of dist. water was shaked for 5 h at room temperature with 850 g of DOWEX 1×4 (Cl form, 50–100 mesh) and the mixture was filtered and washed with water. The filtrate was lyophilized to obtain 17.9 g(84%) of 1-[(2R,3R)-3-[4-(4-cyanophenyl)thiazol-2-yl]-2-hydroxy-2-(2,5-difluorophenyl)butyl]-4-(3,5-dimethyl-4-methylaminoacetoxybenzyl)-1H-[1,2,4]triazol-4-ium chloride hydrochloride as a white solid.

FAB-MS: m/z 643 M$^+$; $^1$H-NMR(DMSO-d): 1.19(3H,d, J=6.9 Hz), 2.11(6H,s), 2.63(3H,s), 4.15(1H,q,J=6.9 Hz), 4.40(2H,s), 4.75,5.04 (2H,ABq,J=14.2 Hz), 5.41(2H,s), 6.86 (1H,brs), 7.11(2H,s), 7.20–7.38(2H,m), 7.94,8.20(4H,ABq, J=8.3), 8.45(1H,s), 9.08(1H,s), 9.66(2H,brs), 10.22(1H,s)

Recrystallization of 1.8 g of 1-[(2R,3R)-3-[4-(4-cyanophenyl)thiazol-2-yl]-2-hydroxy-2-(2,5-difluorophenyl)butyl]-4-(3,5-dimethyl-4-methylaminoacetoxybenzyl)-1H-[1,2,4]triazol-4-ium chloride hydrochloride was done from 1N-HCl (44 mL) to obtain 1.44 g (80%) of 1-[(2R,3R)-3-[4-(4-cyanophenyl)thiazol-2-yl]-2-hydroxy-2-(2,5-difluorophenyl)butyl]-4-(3, 5-dimethyl-4-methylaminoacetoxybenzyl)-1H-[1,2,4]triazol-4-ium chloride hydrochloride as a white crystal.

EXAMPLE 3 a) Preparation of 4-[(R)-2-Hydroxypropionyl] morpholine

A mixture of methyl (R)-lactate (175 g) and morpholine (440 ml, 3 eq) was heated at 85° C. for 40 h. The mixture was evaporated under reduced pressure. Purification of the residue by silica gel chromatography (using n-hexane:ethyl acetate=1:1 ~ethyl acetate as an eluent) gave 4-[(R)-2-hydroxypropionyl]morpholine (232.4 g, 87% yield) as a pale yellow oil.

b) Preparation of 4-[(2R)-2-(3,4,5,6-Tetrahydro-2H-pyran-2-yloxy)propionyl]morpholine 3,4-Dihydro-2H-pyran (90.5 ml, 1.2 eq) was added dropwise to a mixture of 4-[(R)-2-hydroxypropionyl]morpholine (132 g) and p-toluenesulfonic acid monohydrate (500 mg, 0.003 eq) in dry dichloromethane (500 ml) over a period of 15 min with stirring at 0° C. After being stirred for 30 min at 0° C., the mixture was washed with aqueous sodium bicarbonate, dried over anhydrous magnesium sulfate and concentrated under reduced pressure. Purification of the residue by silica gel chromatography, using n-hexane: ethyl acetate (8:1)~ethyl acetate as an eluent, gave 4-[(2R)-2-(3,4,5,6-Tetrahydro-2H-pyran-2-yloxy)propionyl]morpholine (191.6 g, 95% yield) as a pale yellow oil.

EI-MS(+): m/z 243 (M+)

c) Preparation of (2R)-2',4',5'-Trifluoro-2-(3,4,5,6-tetrahydro-2H-pyran-2-yloxy)propiophenone A mixture of magnesium (turnings, 228 mg, 1.2 eq) and 1-bromo-2,4,5-trifluorobenzene (1.1 ml, 1.2 eq) in dry tetrahydrofuran (25 ml) was vigorously stirred for 3 h at room temperature until magnesium was completely dissolved. After the mixture was cooled to −10° C., a solution of 4-[(2R)-2-(3,4,5,6-Tetrahydro-2H -pyran-2-yloxy)propinyl]morpholine (1.9 g) in dry tetrahydrofuran (5 ml) was added dropwise over a period of 5 min. The whole was stirred at r.t. for 24 h. A saturated aqueous solution of ammonium chloride and water were added to the reaction mixture and the resulting mixture was extracted with ethyl acetate. The extracts were combined, washed successively with water and brine and dried over anhydrous magnesium sulfate. The solvent was evaporated off under reduced pressure followed by purification of the residue by silica gel chromatography, using n-hexane:ethyl acetate (30:1~5:1) as an eluent, gave (2R)-2',4',5'-Trifluoro-2-(3,4,5,6-tetrahydro-2H-pyran-2-yloxy)propiophenone (1.8 g, 80% yield) as a pale yellow oil. The product was a mixture of 2 diastereomers.

ESI-MS(+): m/z 289 (MH)+

1H-NMR(CDCl$_3$): 1.42–1.90(9H,m), 3.31–3.93(2H,m), 4.62–5.12(2H,m), 6.95–7.05(1H,m), 6.68–7.78(1H,m)

d) Preparation of 2-(2,4,5-Trifluorophenyl)-2-[(1R)-1-(3,4,5,6-tetrahydro-2H -pyran-2-yloxy)ethyl]oxirane Trimethylsulfoxonium iodide (697 mg, 1.2 eq) was added portionwise to a stirred mixture of sodium hydride [60% mineral oil dispersion] (122 mg, 1.15 eq) and dry dimethyl sulfoxide (7 ml) at 0° C. The resulting mixture was stirred at room temperature for 40 min and then cooled in an ice bath. A solution of (2R)-2',4',5'-trifluoro-2-(3,4,5,6-tetrahydro-2H-pyran-2-yloxy)propiophenone (760 mg) in dry dimethyl sulfoxide (2 ml) was added to the mixture and stirring was continued for 2 h at room temperature. The mixture was poured into ice-water and extracted with ethyl acetate. The organic layer was washed successively with water and brine, and dried over anhydrous sodium sulfate. Evaporation of the solvent gave 2-(2,4,5-trifluorophenyl)-2-[(1R)-1-(3,4,5,6-tetrahydro-2H-pyran-2-yloxy)ethyl]oxirane ( 810 mg) as a pale yellow oil, which was a mixture of 4 diastereomers and was used for the next step without further purification.

e) Preparation of (3R)-2-(2,4,5-Trifluorophenyl)-3-(3,4,5,6-tetrahydro-2H -pyran-2-yloxy)-1-(1H-1,2,4-triazol-1-yl)-2-butanol 1H-1,2,4-Triazole (510 mg) was added portionwise to a mixture of sodium hydride [60% mineral oil dispersion] (264 mg) and dry N,N-dimethylformamide (8 ml) and the mixture was stirred at room temperature for 35 min. A solution of 2-(2,4,5-trifluorophenyl)-2-[(1R)-1-(3,4,5,6-tetrahydro-2H-pyran-2-yloxy)ethyl]oxirane (796 mg) obtained above in dry N,N-dimethylformamide (2 ml) was added to the mixture at room temperature. The resulting mixture was heated at 80° C. for 1.5 h with stirring and after being cooled, the mixture was poured into ice-water and the whole was extracted with ethyl acetate. The extract was washed with water and dried over anhydrous magnesium sulfate. The solvent was evaporated off under reduced pressure and purification of the residue by silica gel chromatography, using n-hexane:ethyl acetate (1:2) as an eluent, gave (3R)-2-(2,4,5-trifluorophenyl)-3-(3,4,5,6-tetrahydro-2H-pyran-2-yloxy)-1-(1H-1,2,4-triazol-1-yl)-2-butanol (760 mg, 78% yield for 2 steps) as a colourless oil. The product was a mixture of 4 diastereomers.

ESI-MS(+): m/z 372 (MH)+

1H-NMR(CDCl$_3$): 1.00–1.35(3H,m), 1.40–1.92(6H,m), 3.39–5.00(7H,m), 6.79–6.91(1H,m), 7.27–7.38(1H,m), 7.74–8.12(2H,m)

f) Preparation of (2R,3R)-2-(2,4,5-Trifluorophenyl)-1-(1H-1,2,4-triazol-1-yl)-2,3-butanediol A mixture of (3R)-2-(2,4,5-trifluorophenyl)-3-(3,4,5,6-tetrahydro-2H-pyran-2-yloxy)-1-(1H-1,2,4-triazol-1-yl)-2-butanol (740 mg) and pyridinium p-toluene sulfonate (PPTS, 200 mg) in ethanol (15 ml) was heated at 55° C. for 7 h. The reaction mixture was partitioned between ethyl acetate and water. The water layer was extracted with ethyl acetate. The combined organic extracts were dried over anhydrous magnesium sulfate, and concentrated to dryness in vacuo. Purification of the residue by silica gel chromatography, using dichloromethane:methanol (20:1) as an eluent, gave (2R,3R)-2-(2,4,5-trifluorophenyl)-1-(1H-1, 2,4-triazol-1-yl)-2,3-butanediol (361 mg, 63%) as white amorphous.

ESI-MS(+): m/z 288 (MH)+

1H-NMR(CDCl$_3$): 0.99(3H,d,J=6.6 Hz), 2.45(1H,br.d), 4.30(1H,m), 4.80(1H,d,J=14.2 Hz), 4.84(1H,d,J=14.2 Hz), 4.88(1H,s), 6.83–6.93(1H,m), 7.29–7.36(1H,m), 7.87(1H,s), 7.88(1H,s)

g) Preparation of (2R,3S)-2-(2,4,5-Trifluorophenyl)-3-methyl-2-(1H-1,2,4-triazol-1-yl)methyloxirane Methanesulfonyl chloride (0.11 ml, 1.1 eq) was added to a mixture of (2R,3R)-2-(2,4,5-trifluorophenyl)-1-(1H-1,2,4-triazol-1-yl)-2,3-butanediol (345 mg) and triethylamine (0.2 ml) in dry ethyl acetate (2 ml) and dry dichloromethane (9 ml) at 0° C. The mixture was stirred at room temperature for 2 h and the reaction mixture was quenched with saturated aqueous solution of sodium chloride. The organic layer was dried over anhydrous sodium sulfate, and evaporation of the solvent under reduced pressure gave the mesylate as an oil. The resulting oil was dissolved in methanol (10 ml) and sodium methoxide [28% in methanol] (0.29 ml) was added to the mixture at 0° C. The mixture was stirred at 0° C. for 30 min and was partitioned between ethyl acetate and water. The organic extract was dried over anhydrous magnesium sulfate and filtered. Evaporation of the solvent and purification of the residue by silica gel chromatography, using dichloromethane:methanol (40:1) as an eluent, gave (2R, 3S)-2-(2,4,5-trifluorophenyl)-3-methyl-2-(1H-1,2,4-triazol-1-yl)methyloxirane (310 mg, 96% ) as a white solid.

ESI-MS(+): m/z 270 (MH)+

1H-NMR(CDCl$_3$): 1.64(3H,d,J=5.6 Hz), 3.19(1H,q,J=5.6 Hz), 4.40(1H,d,J=14.5 Hz), 4.93(1H,d,J=14.5 Hz), 6.85–6.95(2H,m), 7.83(1H,s), 8.02(1H,s)

h) Preparation of (2S,3R)-3-(2,4,5-Trifluorophenyl)-3-hydroxy-2-methyl-4-(1H-1,2,4-triazol-1-yl) butyronitrile A mixture of 295 mg of (2R,3S)-2-(2,4,5-trifluorophenyl)-3-methyl-2-(1H-1,2,4-triazol-1-yl) methyloxirane, 0.59 ml of trimethylsilylcyanide and 222 mg of magnesium oxide (light) in 10 ml of o-xylene was stirred at 130° C. for 23 h. After cooling the mixture was filtered and the filtrate was concentrated to dryness. The resulting oil was dissolved in 10 ml of THF and 0.39 ml of conc. hydrogen chloride was added to the mixture. The mixture was stirred at room temperature for 22 h and was diluted with ethyl acetate and aqueous sodium bicarbonate. The organic extract was dried over anhydrous sodium sulfate and concentrated. Purification of the residue by silica gel chromatography, using dichloromethane:methanol (30:1) as an eluent, gave (2S,3R)-3-(2,4,5-trifluorophenyl)-3-hydroxy-2-methyl-4-(1H-1,2,4-triazol-1-yl)butyronitrile (243mg, 75%) as a white solid.

ESI-MS(+): m/z 297 (MH)+

1H-NMR(CDCl$_3$): 1.19(3H,d,J=7.3 Hz), 3.27(1H,q,J=7.3 Hz), 4.82(1H,d,J=14.2 Hz), 4.96(1H,d,J=14.2 Hz), 5.60(1H, s), 6.85–6.95(1H,m), 7.29–7.37(1H,m), 7.87(1H,s), 7.88 (1H,s)

i) Preparation of (2R,3R)-3-(2,4,5-Trifluorophenyl)-3-hydroxy-2-methyl-4-1H-[1,2,4]triazol-1-yl) thiobutyramide A mixture of 235 mg of (2S,3R)-3-(2,4,5-trifluorophenyl)-3-hydrxy-2-methyl-4-(1H-1,2,4-triazol-1-yl)butyronitrile in 1.5 ml of dithiophosphoric acid O,O-diethyl ester and 0.5 ml of water was stirred at 100° C. for 30 min. After cooling, the mixture was washed with n-hexane and the residue was diluted with ethyl acetate and aqueous sodium bicarbonate. The organic layer was dried over anhydrous sodium sulfate and concentrated. Purification of the residue by silica gel column chromatography, using dichloromethane:methanol (12:1) as an eluent, gave (2R,3R)-3-(2,4,5-trifluorophenyl)-3-hydroxy-2-methyl-4-1H-[1,2,4]triazol-1-yl)thiobutyramide (255 mg, 98%) as a white amorphous.

ESI-MS(+): m/z 331 (MH)+

1H-NMR(CDCl$_3$): 1.13(3H,d,J=7.3 Hz), 3.71(1H,q,J=7.3 Hz), 4.54(1H,d,J=14.5 Hz), 5.06(1H,d,J=14.5 Hz), 5.92(1H, s), 6.83–6.91(1H,m), 7.29–7.38(1H,m), 7.67(1H,br.s), 7.82 (1H,s), 7.88(1H,s), 8.30(1H,br.s)

j) Preparation of 2-Bromo-4'-cyanoacetophenone

To a mixture of para-cyanoacetophenone (52 g, 0.36 mol) in chloroform (520 ml) and 48% HBr (5.2 ml), a solution of bromine (19.3 ml) in chloroform (52 ml) was added dropwise over a period of 20 min. The mixture was stirred for 3 h at room temperature and neutralized to pH7 with sat. NaHCO$_3$. The organic layer was washed with sat. NaCl and dried over anhydrous Na$_2$SO$_4$ and concentrated. The residue was chromatographed on silica gel (AcOEt/n-hexane=1/3 as an eluent) and recrystallized to obtain 2-bromo-4'-cyanoacetophenone as a colourless plate (23.4 g, 29%).

EI-MS(+): m/z 223 (M+)

1H-NMR(CDCl$_3$): 4.43(2H,s), 7.80(2H,d,J=6.6 Hz), 8.09 (2H,d,J=6.6 Hz)

k) Preparation of (1R,2R)-4-[2-[2-Hydroxy-1-methyl-3-[1,2,4]triazol-1-yl-2-(2,4,5-trifluorophenyl) propyl]thiazol-4-yl]benzonitrile A mixture of 188 mg of (2R,3R)-3-(2,4,5-trifluorophenyl)-3-hydroxy-2-methyl-4-1H-[1,2,4]triazol-1-yl)thiobutyramide and 141 mg of 2-bromo-4'-cyanoacetophenone in 4 ml of acetonitrile was stirred for 22 h at room temperature. The mixture was diluted with ethyl acetate and was washed with aqueous sodium bicarbonate. The organic layer was dried over anhydrous sodium sulfate and concentrated. Purification of the residue by silica gel column chromatography, using dichloromethane:ethyl acetate (3:1) as an eluent, gave (1R,2R)-4-[2-[2-hydroxy-1-methyl-3-[1,2,4]triazol-1-yl-2-(2,4,5-trifluorophenyl) propyl]thiazol-4-yl]benzonitrile (212 mg, 82%) as a white solid.

ESI-MS(+): m/z 456 (MH)+

1H-NMR(CDCl$_3$): 1.25(3H,d,J=7.3 Hz), 4.08(1H,q,J=7.3 Hz), 4.25(1H,d,J=14.2 Hz), 4.91(1H,d,J=14.2 Hz), 5.88(1H, s), 6.89–6.99(1H,m), 7.35–7.45(1H,m), 7.65(1H,s), 7.71 (1H,s) 7.75(2H,d,J=8.3 Hz), 7.88(1H,s), 8.02(2H,d,J=8.4 Hz)

l) Preparation of (tert-Butoxycarbonylmethylamino) acetic acid 4-bromomethyl-2,6-dimethylphenyl ester To a solution of 1.35 g of 3,5-dimethyl-4-hydroxybenzaldehyde, 1.73 g of N-(tert-butoxycarbonyl) sarcosine and 0.2 g of 4-(N,N-dimethylamino)pyridine in 20 ml of dichloromethane was added 1.9 g of 1-(3-dimethylaminopropyl)-3-ethylcarbodiimide hydrochloride and stirring was continued for 2.5 h at room temperature. The mixture was diluted with ethyl acetate and was washed with 0.25N HCl. The organic layer was dried over anhydrous sodium sulfate and concentrated to obtain 4-(tert-butoxycarbonylmethylamino)acetoxy-3,5-dimethylbenzaldehyde (2.9 g) as a yellow oil.

A mixture of 2.88 g of 4-(tert-butoxycarbonylmethylamino)acetoxy-3,5-dimethylbenzaldehyde and 0.34 g of sodium borohydride in 25 ml of tetrahydrofuran was stirred for 2 h at room temperature. The mixture was diluted with ethyl acetate and was washed with 0.25N HCl. The organic layer was dried over anhydrous sodium sulfate and concentrated to obtain (tert-butoxycarbonylmethylamino)acetic acid 2,6-dimethyl-4-hydroxymethylphenyl ester (2.9 g) as a colourless syrup. To a solution of 2.8 g of (tert-butoxycarbonylmethylamino) acetic acid 2,6-dimethyl-4-hydroxymethylphenyl ester and 2.73 g of triphenylphosphine in 30 ml of dichloromethane, 3.44 g of carbon tetrabromide was added and the mixture was stirred for 1 h at room temperature. The mixture was concentrated and the residue was chromatographed on silica gel (Wakogel C-200, solvent: CH$_2$Cl$_2$)to obtain (tert-butoxycarbonylmethylamino)acetic acid 4-bromomethyl-2, 6-dimethylphenyl ester (2.97 g, 89% ) as a colourless oil.

FAB-MS(+): m/z 386 (MH)+

1H-NMR(CDCl$_3$) 1.48(9H,s) 2.15(6H,s), 3.02(3H,s), 4.23(2H,br.d), 4.43(2H,s), 7.11 (2br.s)

m) Preparation of (2R,3R)-4-[4-(N-tert-Butoxycarbonyl-N-methylaminoacetoxy)-3,5-dimethylbenzyl]-1-[3-[4-(4-cyanophenyl)thiazol-2-yl]-2-hydroxy-2-(2,4,5-trifluorophenyl)butyl]-1H-[1,2,4]triazol-4-ium bromide A mixture of 140 mg of (1R,2R)-4-[2-2-hydroxy-1-methyl-3-[1,2,4]triazol-1-yl-2-(2,4,5-trifluorophenyl)

propyl]thiazol-4-yl]benzonitrile and 131 mg of (tert-butoxycarbonylmethylamino)acetic acid 4-bromomethyl-2,6-dimethylphenyl ester, prepared above, in 5 mL of acetonitrile was stirred for 20 h at reflux and concentrated. The residue was chromatographed on silica gel (Wakogel C-200, solvent: $CH_2Cl_2/MeOH=12/1$) to obtain 178 mg(69%) of (2R,3R)-4-[4-(N-tert-butoxycarbonyl-N-methylaminoacetoxy) -3,5-dimethylbenzyl]-1-[3-[4-(4-cyanophenyl)thiazol-2-yl]-2-hydroxy-2-(2,4,5-trifluorophenyl)butyl]-1H-[1,2,4]triazol-4-ium bromide as a white solid.

FAB-MS(+): m/z 761 (M)+

1H-NMR($CDCl_3$): 1.23(3H,d,J=7.5 Hz), 1.47(9H,s) 2.14 (6H,s), 3.02(3H,s), 4.10(1H,q,J=7.5 Hz), 4.25(2H,s), 5.02 (1H,d,J=14.2 Hz), 5.14(1H,d,J=14.2 Hz), 5.37–5.54(2H,m), 6.31(1H,s), 6.92–7.02(1H,m), 7.08(2H,br.d), 7.36–7.46(1H, m), 7.58(1H,br.s), 7.73(2H,d,J=8.4 Hz), 8.01(1H,s), 8.05 (2H,d,J=8.4 Hz), 11.36(1H,s)

n) Preparation of 1-[(2R,3R)-3-[4-(4-Cyanophenyl) thiazol-2-yl]-2-hydroxy-2-(2,4,5-trifluorophenyl) butyl]-4-(3,5-dimethyl-4-methylaminoacetoxybenzyl)-1H-[1,2,4]triazol-4-ium A mixture of 167 mg of (2R,3R)-4-[4-(N-tert-butoxycarbonyl-N-methylaminoacetoxy)-3,5-dimethylbenzyl]-1-[3-[4-(4-cyanophenyl)thiazol-2-yl]-2-hydroxy-2-(2,4,5-trifluorophenyl)butyl]-1H-[1,2,4]triazol-4-ium bromide and 2 ml of 4N-HCl in ethyl acetate in 4 ml of ethyl acetate was stirred for 4 h at room temperature and filtered. The white solid was washed with ether and dried in vacuo to obtain 141 mg(92%) of 1-[(2R,3R)-3-[4-(4-cyanophenyl)thiazol-2-yl]-2-hydroxy-2-(2,4,5-trifluorophenyl)butyl]-4-(3,5-dimethyl-4-methylaminoacetoxybenzyl)-1H-[1,2,4]triazol-4-ium bromide hydrochloride.

FAB-MS(+): m/z 661 (M)+

1H-NMR(DMSO-d6): 1.21(3H,d,J=7.3 Hz), 2.11(6H,s), 2.64(3H,br.t), 4.12(1H,q,J=7.3 Hz), 4.42(2H,br.t), 4.74(1H, d,J=14.2 Hz), 5.02(1H,d,J=14.2 Hz), 5.41(2H,s), 6.87(1H,s), 7.13(2H,s), 7.26–7.36(1H,m), 7.62–7.73(1H,m), 7.94(2H,d, J=8.6 Hz), 8.21(2H,d,J=8.6 Hz), 8.46(1H,s), 9.08(1H,s), 9.51(2H,br.s), 10.19(1H,s)

EXAMPLE 4 a) Preparation of (2R)-2',5'-difluoro-2-(3,4,5,6-tetrahydro-2H-pyran-2-yloxy)-propiophenone A mixture of magnesium (7.25 g, 0.298 mol) and iodine (catalytic amount) and 1-bromo-2,5-difluorobenzene (20.0 g, 0.178 mol) in THF (250 ml) was vigorously stirred. The color of iodine was disappeared and the inner temperature rose up to 65° C. To this mixture was added additional 1-bromo-2,5-difluorobenzene (30.0 g, 0.267 mol) dropwise to maintain the inner temperature from 50 to 55° C. over 45 min. The resulting mixture was stirred at 55° C. for 30 min. then at r.t. for 1 hr. The mixture was cooled down to −5° C. To this mixture was added a solution of 4-[(2R)-2-(3,4,5,6-Tetrahydro-2H-pyran-2-yloxy)propionyl]morpholine (52.5 g, 0.216 mol) in THF (150 ml) dropwise over 40 min. And the resulting mixture was stirred at r.t. for 4 hrs. The reaction mixture was cooled down to 5° C. and saturated $NH_4Cl$ aq. (100 ml) was added carefully. The whole was diluted with $H_2O$ (600 ml) and extracted with EtOAc (400 ml+200 ml×2). The combined organic layer was dried over $Na_2SO_4$ and concentrated in vacuo. The residue was chromatographed on silica gel (n-hexane:EtOAc=10:1~5:1) to give (2R)-2',5'-Difluoro-2-(3,4,5,6-tetrahydro-2H-pyran-2-yloxy)-propiophenone (47.3 g, 81%) as pale yellow syrup.

Physical form: colorless oil; FAB-MS: m/z 271(M+H)+; 1H-NMR(CDCl3) δ1.42~1.90(9H,m),3.32~3.40(1H×½,m), 3.69~3.77(1H×½,m),3.86~3.94(1H×½,m), 4.66(1H×½,t,J= 3.6 Hz),4.75(1H×½,t,J=3.6 Hz),4.87(1H×½,q,J=6.6 Hz), 5.11(1H×½,q,J=6.9 Hz),7.08~7.25(2H,m),7.49~7.55(1 H,m).

b) Preparation of 2-(2,5-difluorophenyl)-2-[(1R)-1-(3,4,5,6,-tetrahydro-2H -pyran-2-yloxy)ethyl] oxirane 1) NaH (42.3 g, 60% in mineral oil, 1.06 mol), placed in a 3 L three-neck round bottle flask, was washed with hexane (100 mL×3) and dried in vacuo. DMSO (500 mL, dried over 3A molcular sieves) was added under $N_2$ atmosphere and the resulting suspension was cooled in an ice-water bath. Trimethylsulfoxonium iodide (275.2 g, 1.25 mol) was added portionwise over a period of 30 min (caution: addition of a large quantity of sulfoxonium iodide in one portion causes vigorous hydrogen gas evolution and temperature raising.). After stirring for half an hour at 0° C., the mixture was allowed to warm to room temperature and stirred for 1 h. To the resulting viscous suspension was added dry THF (1 L), and the mixture was stirred for further 1 h at room temperature. A solution of (2R)-2',5'-Difluoro-2-(3,4,5,6-tetrahydro-2H-pyran-2-yloxy)-propiophenone (260 g, 0.962 mol) in dry THF (500 mL) was added via cannula over a period of 30 min and the mixture was stirred for 2 h at room temperature. Water (1 L) was added to quench the reaction and the mixture was extracted with AcOEt (500 mL×3). AcOEt layer was combined and washed with brine (500 mL×2), dried over $MgSO_4$ and evaporated in vacuo to give crude product. $^1$H NMR spectrum indicated the diastereomeric ratio is ca. 6:1.

2) To a suspension of trimethylsulfoxonium iodide (147.5 g, 670 mmol) in anhydrous THF(600 ml) was added n-BuLi (427 ml, 1.57M in hexane, 670 mmol) at 0° C. dropwisely. After the addition was complete, the reaction mixture was warmed to room temperature, stirred for 30 minutes. The mixture was cooled to 0° C. and DMPU (130 ml) was added, followed by dropwise addition of (2R)-2',5'-Difluoro-2-(3, 4,5,6-tetrahydro-2H-pyran-2-yloxy)-propiophenone (150 g, 550 mmol) from a droping funnel. The funnel was washed with THF (60 ml). After the addition was complete, the reaction mixture was warmed to room temperature and stirred overnight. The mixture was extracted with ethyl acetate/hexane (1/1), washed with water, brine. The combined organic phase was dried ($Na_2SO_4$), filtered, concentrated to give a residue. The residue was filtered through a short $SiO_2$ column (EtOAc/hexane=1/10). The solvent was removed and the product was dried with high vacum pump overnight(98 g, 63%, diastereoselectivity: 15:1).

Physical form: pale yellow syrup, EI-MS: m/z 284 (M)+; $^1$H-NMR(CDCl3) δ1.15(3H×½,dd,J=6.6,1.3 Hz), 1.24(3H× ½,dd,J=6.6,1.3 Hz), 1.52~1.87(6H,m),2.83~2,90(1H,m), 3.07(1H×½,d,J=5.3 Hz),3.36(1H×½,d,J=5.6 Hz),3.48~3.56 (1H,m),3.82~3.92(1H,m),4.00~4.16(1H,m),4.73~4.92(1H, m),6.96~7.02(1H,m),7.09~7.15(1H,m).

c) Preparation of (2R,3R)-2-(2,5-difluorophenyl)-1-(1H-1,2,4-triazol-1-yl)-2,3-butanediol 1) To a suspension of NaH (38.5 g, 60% in mineral oil, 0.962 mol, washed with hexane three times) in DMF (1 L) cooled in an ice-bath was added triazole (133 g, 1.92 mol) portionwise over a period of 30 min. After completion of the addition, the mixture was warmed to room temperature. The above crude 2-(2,5-Difluorophenyl)-2-[(1R)-1-(3,4,5,6,-tetrahydro-2H-pyran-2-yloxy)ethyl]oxirane was added and the mixture was heated at 70° C. for 8 h. After cooling to room temperature, the reaction mixture was quenched with water (1 L) and the mixture was extracted with EtOAc (1 L×3). The EtOAc layer was combined and washed with water and brine, dried over MgSO$_4$, and evaporated under reduced pressure. The portion of residue was chromatographed on silicagel for analysis (n-hexane: EtOAc= 4:1~1:5) to give pure (3R)-2-(2,5-difluorophenyl)-3-(3,4,5,6-tetrahydro-2H-pyran-2-yloxy)-1-(1H-1,2,4-triazol-1-yl)-2-butanol.

Physical form: colorless syrup; FAB-MS: m/z 354 (M+H)$^+$; $^1$H-NMR(CDCl$_3$) δ1.00(3H×½,d,J=6.6 Hz),1.13 (3H×½,d,J=6.6 Hz),1.42~1.88(6H,m),3.38 ~3.60(1H,m), 3.80~4.00(1H,m),4.32~5.02(5H,m),6.83~6.99(2H,m), 7.14~7.21(1H,m),7.73(1H×½,s),7.74(1H×½,s),7.92(1H×½,s),7.95(1H×½,s).

2) The crude residue without purification was dissolved in MeOH (250 mL) and hexane (1 L) and 0.5 N aqueous HCl solution (1 L) were added (please make sure the aqueous phase is acidic). The mixture was stirred for 2 h at room temperature (the solution became clear two phases). The organic layer was removed and the aqueous layer was washed with hexane (500 mL×2), and combined hexane layer was extracted with water (500 mL). Aqueous phases were combined and basified by adding solid Na$_2$CO$_3$ (26 g) with cooling in an ice-bath. The resulting heterogeneous mixture was extracted with EtOAc (1 L×3) and combined EtOAc layer was washed with brine (500 mL×2), dried over MgSO$_4$ and evaporated under reduced pressure. The obtaining residue was purified by silica gel column chromatography (eluent: CH$_2$Cl$_2$ only to CH$_2$Cl$_2$/EtOH=20/1). Fractions containing the desired diastereoisomer as the major were combined and evaporated under reduced pressure to give crude product (159 g). The product was dissolved in refluxing t-BuOMe (700 mL). Insoluble white powdery crystal (heterodimer) was removed by filtration and the filtrate was concentrated under reduced pressure. The resulting solid was recrystalized from t-BuOMe-hexane to give pure (2R,3R)-2-(2,5-difluorophenyl)-1-(1H-1,2,4-triazol-1-yl)-2,3-butanediol (110 g, 42% over 3 steps).

Physical form: colorless syrup; FAB-MS: m/z 270 (M+H)$^+$; $^1$H-NMR(CDCl$_3$) δ0.99(3H,d,J=6.6 Hz),2.61(1H, d,J=10.6 Hz),4.31~4.36(1H,m),4.79,4.88(2H,ABq,J=14.5 Hz),4.84(1H,s),6.84~6.99(2H,m),7.13~7.19(1H,m),7.84 (1H,s),7.85(1H,s).

d) Preparation of (2R,3S)-2-(2,5-difluorophenyl)-3-methyl-2-[(1H-1,2,4-triazol-1-yl)-methyl]-oxirane To a solution of (2R,3R)-2-(2,5-difluorophenyl)-1-(1H-1,2,4-triazol-1-yl)-2,3-butanediol (53.0 g, 197 mmol) and Et$_3$N (54.8 mL, 394 mmol) in CH$_2$Cl$_2$-EtOAc (1:3, 400 mL) cooled in an ice-bath was added MsCl (17.5 mL, 227 mmol) dropwise over a period of 15 min. After stirring for 30 min at 0° C., the mixture was warmed to room temperature and quenched with water (200 mL). EtOAc (200 mL) was added and the organic layer was washed with water and brine, dried over MgSO$_4$ and evaporated under reduced pressure. The obtaining residue was dissolved in MeOH (500 mL) and cooled in an ice-bath. A solution of NaOMe (41.8 g, 28% in MeOH, 217 mmol) was added dropwise and after the completion of the addition, the mixture was stirred for 15 min at 0° C. MeOH was evaporated under reduced pressure and the resulting residue was dissolved in EtOAc (500 mL).

The EtOAc solution was washed with water and brine, dried over MgSO$_4$ and evaporated under reduced pressure. The obtaining solid was recrystalized from t-BuOMe-hexane to give pure (2R,3S)-2-(2,5-Difluorophenyl)-3-methyl-2-[(1H-1,2,4-triazol-1-yl)-methyl]-oxirane (43.5 g, 88%).

Physical form: white solid; FAB-MS: m/z 252 (M+H)$^+$; $^1$H-NMR(CDCl$_3$) δ1.64(3H,d,J=5.6 Hz),3.19(1H,q,J=5.6 Hz),4.42,4.97(2H,ABq,J=14.8 Hz),6.75~6.81(1H,m), 6.89~7.01(2H,m),7.83(1H,s),7.98(1H,s).

e) Preparation of (2S,3R)-3-(2,5-difluoro-phenyl)-3-hydroxy-2-methyl-4-[1,2,4]triazol-1-yl-butyronitrile To a solution of acetone cyanohydrin (61.0 mL, 600 mmol) in dry THF (500 mL) cooled in an ice-bath was added LiH (4.77 g, 600 mmol) portionwise. After stirring for 1 h at 0° C., the mixture was warmed to room temperature and stirred further for 1 h. (2R,3S)-2-(2,5-Difluorophenyl)-3-methyl-2-[(1H-1,2,4-triazol-1-yl)-methyl]-oxirane (50.0 g, 199 mmol) was added and the mixture was heated to reflux for 4 h. After approx. 300 mL of THF was distilled out under atmospheric pressure, the mixture was cooled in an ice-bath and quenched with water (250 mL). The mixture was extracted with EtOAc (600 mL) and the EtOAc layer was washed with water (200 mL×4) and brine (200 mL×2), dried over MgSO$_4$ and evaporated. The obtaining solid was recrystalized from isopropanol-hexane to give pure (2S,3R)-3-(2,5-Difluoro-phenyl)-3-hydroxy-2-methyl-4-[1,2,4]triazol-1-yl-butyronitrile (45.9 g, 83%).

Physical form: colorless syrup; FAB-MS: m/z 279 (M+H)$^+$; $^1$H-NMR(CDCl3) δ1.19(3H,d,J=7.3 Hz),3.33(1H, q,J=7.3 Hz),4.82,5.00(2H,ABq,J=13.9 Hz),5.56(1H,brs), 6.89~7.04(2H,m),7.12~7.19(1H,m),7.85(1H,s),7.86(1H,s).

f) Preparation of (2R,3R)-3-(2,5-difluoro-phenyl)-3-hydroxy-2-methyl-4-[1,2,4]triazol-1-ylthiobutyramide (2S,3R)-3-(2,5-Difluoro-phenyl)-3-hydroxy-2-methyl-4-[1,2,4]triazol-1-yl-butyronitrile (50.0 g, 180 mmol), diethyl dithiophosphate (134 mL, 719 mmol), isopropanol (50 mL) and water (40 mL) were mixed together and the mixture was heated in an oil-bath (temp. setting at 110° C.) for 3 h. After cooling to 0° C., 5% Na$_2$CO$_3$ aqueous solution (500 mL) was added slowly and then solid Na$_2$CO$_3$ (25 g) was added portionwise. The mixture was extracted with EtOAc (1 L) and the EtOAc layer was washed with sat. NaHCO$_3$ aqueous solution, water (×2) and brine, dried over MgSO$_4$ and evaporated under reduce pressure. The resulting solid was purified by recrystalization from isopropanol to give pure (2R,3R)-3-(2,5-difluoro-phenyl)-3-hydroxy-2-methyl-4-[1, 2,4]triazol-1-ylthiobutyramide (47.9 g, 85%).

Physical form: White solid; FAB-MS: m/z 313 (M+H)$^+$; $^1$H-NMR(CDCl$_3$) δ1.12(3H,d,J=7.3 Hz),3.74(1H,q,J=7.3 Hz),4.55,5.12(2H,ABq,J=14.5 Hz),5.84(1H,s),6.85~7.02 (2H,m),7.15~7.22(1H,m),7.80(1H,s),7.89(1H,s),7.89(1H, brs),8.43(1H,brs).

g) Preparation of 2-bromo-4'-cyanoacetophenone

To a mixture of para-cyanoacetophenone (52 g, 0.36 mol) in chloroform (520 ml) and 48% HBr (5.2 ml), a solution of bromine (19.3 ml) in chloroform (52 ml) was added dropwise over a period of 20 min. The mixture was stirred for 3 h at room temperature and neutralized to pH7 with sat. NaHCO$_3$. The organic layer was washed with sat. NaCl and dried over anhydrous Na$_2$SO$_4$ and concentrated. The residue was chromatographed on silica gel (AcOEt/n-hexane=1/3 as an eluent) and recrystallized to obtain 2-bromo-4'-cyanoacetophenone as a colourless plate (23.4 g, 29%).

EI-MS(+): m/z 223 (M+)

1H-NMR(CDCl3) δ4.43(2H,s), 7.80(2H,d,J=6.6 Hz), 8.09(2H,d,J=6.6 Hz)

h) Preparation of (2R,3R)-3-[4-(4-cyanophenyl)thiazol-2-yl)]-2-(2,5-difluorophenyl)-1-(1H-1,2,4-triazol-1-yl)-butan-2-ol To a solution of (2R,3R)-3-(2,5-difluoro-phenyl)-3-hydroxy-2-methyl-4-[1,2,4]triazol-1-ylthiobutyramide (106 g, 340 mmol) in EtOH (500 mL) warmed at 50° C. in a water-bath was added 4-cyano-2'-bromoacetophenone (78.4 g, 350 mmol) portionwise over a period of 15 min and the mixture was stirred for 2 h at 50° C. After evaporation of EtOH under reduced pressure, the residue was dissolved in EtOAc (1.2 L) and the solution was washed with sat. NaHCO₃ and brine, dried over MgSO₄ and evaporated under reduced pressure. The residue was purified by column chromatography followed by trituration with t-BuOMe to give pure (2R,3R)-3-[4-(4-cyanophenyl)thiazol-2-yl)]-2-(2,5-difluorophenyl)-1-(1H-1,2,4-triazol-1-yl)-butan-2-ol (117 g, 79%) as a white powdery crystal.

Physical form: colorless heavy syrup; ESI-MS: m/z 437 (M)+; $^1$H-NMR(CDCl$_3$) δ1.25(3H,d,J=7.3 Hz),4.12(1H,q,J= 7.3 Hz),4.26,4.96(2H,ABq,J=14.5 Hz),5.75(1H,s), 6.89~7.07(2H,m),7.23~7.29(1H,m),7.65(1H,s),7.71(1H,s), 7.75,8.02(4H,ABq,J=8.6 Hz),7.85(1H,s).

EXAMPLE 5 a) Preparation of (2R)-2',4',5'-trifluoro-2-(3,4,5,6-tetrahydro-2H-pyran-2-yloxy) propiophenone A mixture of magnesium (turnings, 228 mg, 1.2 eq) and 1-bromo-2,4,5-trifluorobenzene (1.1 ml, 1.2 eq) in dry tetrahydrofuran (25 ml) was vigorously stirred for 3 h at room temperature until magnesium was completely dissolved. After the mixture was cooled to –10° C., a solution of 4-[(2R)-2-(3,4,5,6-tetrahydro-2H-pyran-2-yloxy)propinyl] morpholine (1.9 g) in dry tetrahydrofuran (5 ml) was added dropwise over a period of 5 min. The whole was stirred at r.t. for 24 h. A saturated aqueous solution of ammonium chloride and water were added to the reaction mixture and the resulting mixture was extracted with ethyl acetate. The extracts were combined, washed successively with water and brine and dried over anhydrous magnesium sulfate. The solvent was evaporated off under reduced pressure followed by purification of the residue by silica gel chromatography (using n-hexane:ethyl acetate=30:1~5:1 as an eluent) gave (2R)-2',4',5'-trifluoro-2-(3,4,5,6-tetrahydro-2H-pyran-2-yloxy) propiophenone (1.8 g, 80% yield) as a pale yellow oil. The product was a mixture of 2 diastereomers.

ESI-MS(+): m/z 289 (MH)+

1H-NMR(CDCl3) δ1.42–1.90(9H,m), 3.31–3.93(2H,m), 4.62–5.12(2H,m), 6.95–7.05(1H,m),6.68–7.78(1H,m)

b) Preparation of 2-(2,4,5-trifluorophenyl)-2-[(1R)-1-(3,4,5,6-tetrahydro-2H-pyran-2-yloxy)ethyl] oxirane Trimethylsulfoxonium iodide (697 mg, 1.2 eq) was added portionwise to a stirred mixture of sodium hydride [60% mineral oil dispersion] (122 mg, 1.15 eq) and dry dimethyl sulfoxide (7 ml) at 0° C. The resulting mixture was stirred at room temperature for 40 min and then cooled in an ice bath. A solution of (2R)-2',4',5'-trifluoro-2-(3,4,5,6-tetrahydro-2H-pyran-2-yloxy)propiophenone (760 mg) in dry dimethyl sulfoxide (2 ml) was added to the mixture and stirring was continued for 2 h at room temperature. The mixture was poured into ice-water and extracted with ethyl acetate. The organic layer was washed successively with water and brine, and dried over anhydrous sodium sulfate. Evaporation of the solvent gave 2-(2,4,5-trifluorophenyl)-2-[(1R)-1-(3,4,5,6-tetrahydro-2H-pyran-2-yloxy)ethyl] oxirane (810 mg) as a pale yellow oil, which was a mixture of 4 diastereomers and was used for the next step without further purification.

c) Preparation of (3R)-2-(2,4,5-trifluorophenyl)-3-(3,4,5,6-tetrahydro-2H-pyran-2-yloxy)-1-(1H-1,2,4-triazol-1-yl)-2-butanol 1H-1,2,4-Triazole (510 mg) was added portionwise to a mixture of sodium hydride [60% mineral oil dispersion] (264 mg) and dry N,N-dimethylformamide (8 ml) and the mixture was stirred at room temperature for 35 min. A solution of 2-(2,4,5-trifluorophenyl)-2-[(1R)-1-(3,4,5,6-tetrahydro-2H-pyran-2-yloxy)ethyl]oxirane (796 mg) obtained above in dry N,N-dimethylformamide (2 ml) was added to the mixture at room temperature. The resulting mixture was heated at 80° C. for 1.5 hr. with stirring and after being cooled, the mixture was poured into ice-water and the whole was extracted with ethyl acetate. The extract was washed with water and dried over anhydrous magnesium sulfate. The solvent was evaporated off under reduced pressure and purification of the residue by silica gel chromatography (using n-hexane:ethyl acetate=1:2 as an eluent) gave (3R)-2-(2,4,5-trifluorophenyl)-3-(3,4,5,6-tetrahydro-2H-pyran-2-yloxy)-1-(1H-1,2,4-triazol-1-yl)-2-butanol (760 mg, 78% yield for 2 steps) as a colourless oil. The product was a mixture of 4 diastereomers.

ESI-MS(+): m/z 372 (MH)+

1H-NMR(CDCl3) δ1.00–1.35(3H,m), 1.40–1.92(6H,m), 3.39–5.00(7H,m), 6.79–6.91(1H,m), 7.27–7.38(1H,m), 7.74–8.12(2H,m)

d) Preparation of (2R,3R)-2-(2,4,5-trifluorophenyl)-1-(1H-1,2,4-triazol-1-yl)-2,3-butanediol A mixture of (3R)-2-(2,4,5-trifluorophenyl)-3-(3,4,5,6-tetrahydro-2H-pyran-2-yloxy)-1-(1H-1,2,4-triazol-1-yl)-2-butanol (740 mg) and pyridinium p-toluene sulfonate (PPTS) 200 mg in ethanol (15 ml) was heated at 55° C. for 7 h. The reaction mixture was partitioned between ethyl acetate and water. The water layer was extracted with ethyl acetate. The combined organic extracts were dried over anhydrous magnesium sulfate, and concentrated to dryness in vacuo. Purification of the residue by silica gel chromatography (using dichloromethane:methanol=20:1 as an eluent) gave (2R,3R)-2-(2,4,5-trifluorophenyl)-1-(1H-1,2,4-triazol-1-yl)-2,3-butanediol (361 mg, 63%) as white amorphous.

ESI-MS(+): m/z 288 (MH)+

1H-NMR(CDCl3) δ0.99(3H,d,J=6.6 Hz), 2.45(1H,br.d), 4.30(1H,m), 4.80(1H,d,J=14.2 Hz), 4.84(1H,d,J=14.2 Hz), 4.88(1H,s), 6.83–6.93(1H,m), 7.29–7.36(1H,m), 7.87(1H,s), 7.88(1H,s)

e) Preparation of (2R,3S)-2-(2,4,5-trifluorophenyl)-3-methyl-2-(1H-1,2,4-triazol-1-yl)methyloxirane Methanesulfonyl chloride (0.11 ml, 1.1 eq) was added to a mixture of (2R,3R)-2-(2,4,5-trifluorophenyl)-1-(1H-1,2,4-triazol-1-yl)-2,3-butanediol (345 mg) and triethylamine (0.2 ml) in dry ethyl acetate (2 ml) and dry dichloromethane (9 ml) at 0° C. The mixture was stirred at room temperature for 2 h and the reaction mixture was quenched with saturated aqueous solution of sodium chloride. The organic layer was dried over anhydrous sodium sulfate, and evaporation of the solvent under reduced pressure gave the mesylate as an oil. The resulting oil was dissolved in methanol (10 ml) and sodium methoxide [28% in methanol] (0.29 ml) was added to the mixture at 0° C. The mixture was stirred at 0° C. for 30 min and was partitioned between ethyl acetate and water. The organic extract was dried over anhydrous magnesium sulfate and filtered. Evaporation of the solvent and purification of the residue by silica gel chromatography (using dichloromethane:methanol=40:1 as an eluent) gave (2R,3S)-2-(2,4,5-trifluorophenyl)-3-methyl-2-(1H-1,2,4-triazol-1-yl)methyloxirane (310 mg, 96%) as a white solid.

ESI-MS(+): m/z 270 (MH)+

1H-NMR(CDCl3) δ1.64(3H,d,J=5.6 Hz), 3.19(1H,q,J=5.6 Hz), 4.40(1H,d,J=14.5 Hz), 4.93(1H,d,J=14.5 Hz), 6.85–6.95(2H,m), 7.83(1H,s), 8.02(1H,s)

f) Preparation of (2S,3R)-3-(2,4,5-trifluorophenyl)-3-hydroxy-2-methyl-4-(1H-1,2,4-triazol-1-yl) butyronitrile A mixture of 295 mg of (2R,3S)-2-(2,4,5-trifluorophenyl)-3-methyl-2-(1H-1,2,4-triazol-1-yl)methyloxirane, 0.59 ml of trimethylsilylcyanide and 222 mg of magnesium oxide (light) in 10 ml of o-xylene was stirred at 130° C. for 23 h. After cooling the mixture was filtered and the filtrate was concentrated to dryness. The resulting oil was dissolved in 10 ml of THF and 0.39 ml of conc.hydrogen chloride was added to the mixture. The mixture was stirred at room temperature for 22 h and was diluted with ethyl acetate and aqueous sodium bicarbonate. The organic extract was dried over anhydrous sodium sulfate and concentrated. Purification of the residue by silica gel chromatography (using dichloromethane:methanol=30:1 as an eluent) gave (2S,3R)-3-(2,4,5-trifluorophenyl)-3-hydroxy-2-methyl-4-(1H-1,2,4-triazol-1-yl)butyronitrile (243 mg, 75%) as a white solid.

ESI-MS(+): m/z 297 (MH)+

1H-NMR(CDCl3) δ1.19(3H,d,J=7.3 Hz), 3.27(1H,q,J=7.3 Hz), 4.82(1H,d,J=14.2 Hz), 4.96(1H,d,J=14.2 Hz), 5.60 (1H,s), 6.85–6.95(1H,m), 7.29–7.37(1H,m), 7.87(1H,s), 7.88(1H,s)

g) Preparation of (2R,3R)-3-(2,4,5-trifluorophenyl)-3-hydroxy-2-methyl-4-1H-[1,2,4]triazol-1-yl) thiobutyramide A mixture of 235 mg of (2S,3R)-3-(2,4,5-trifluorophenyl)-3-hydroxy-2-methyl-4-(1H-1,2,4-triazol-1-yl)butyronitrile in 1.5 ml of dithiophosphoric acid O,O-diethyl ester and 0.5 ml of water was stirred at 100° C. for 30 min. After cooling, the mixture was washed with n-hexane and the residue was diluted with ethyl acetate and aqueous sodium bicarbonate. The organic layer was dried over anhydrous sodium sulfate and concentrated. Purification of the residue by silica gel column chromatography (using dichloromethane:methanol=12:1 as an eluent) gave (2R,3R)-3-(2,4,5-trifluorophenyl)-3-hydroxy-2-methyl-4-1H-[1,2,4]triazol-1-yl)thiobutyramide (255 mg, 98%) as a white amorphous.

ESI-MS(+): m/z 331 (MH)+

1H-NMR(CDCl3) δ1.13(3H,d,J=7.3 Hz), 3.71(1H,q,J=7.3 Hz), 4.54(1H,d,J=14.5 Hz), 5.06(1H,d,J=14.5 Hz), 5.92 (1H,s), 6.83–6.91(1H,m), 7.29–7.38(1H,m), 7.67(1H,br.s), 7.82(1H,s), 7.88(1H,s), 8.30(1H,br.s)

h) Preparation of (2R,3R)-3-[4-(4-cyanophenyl) thiazol-2-yl)]-1-(1H-1,2,4-triazol-1-yl)-2-(2,4,5-trifluorophenyl)-butan-2-ol A mixture of 188 mg of (2R,3R)-3-(2,4,5-trifluorophenyl)-3-hydroxy-2-methyl-4-1H-[1,2,4]triazol-1-yl)thiobutyramide and 141 mg of 2-bromo-4'-cyanoacetophenone in 4 ml of acetonitrile was stirred for 22 h at room temperature. The mixture was diluted with ethyl acetate and was washed with aqueous sodium bicarbonate. The organic layer was dried over anhydrous sodium sulfate and concentrated. Purification of the residue by silica gel column chromatography (using dichloromethane:ethyl acetate=3:1 as an eluent) gave (2R,3R)-3-[4-(4-cyanophenyl)thiazol-2-yl)]-1-(1H-1,2,4-triazol-1-yl)-2-(2,4,5-trifluorophenyl)-butan-2-ol (212 mg, 82%) as a white solid.

ESI-MS(+): m/z 456 (MH)+

1H-NMR(CDCl3) δ1.25(3H,d,J=7.3 Hz), 4.08(1H,q,J=7.3 Hz), 4.25(1H,d,J=14.2 Hz), 4.91(1H,d,J=14.2 Hz), 5.88 (1H,s), 6.89–6.99(1H,m), 7.35–7.45(1H,m), 7.65(1H,s), 7.71(1H,s) 7.75(2H,d,J=8.3 Hz), 7.88(1H,s), 8.02(2H,d,J=8.4 Hz)

EXAMPLE 6

Preparation of (2R,3R)-3-[4-(4-cyanophenyl) thiazol-2-yl)]-2-(3-fluorophenyl)-1-(1H-1,2,4-triazole-1-yl)-butan-2-ol This compound was synthesized by modifying the procedure of Example 4 or 5, such modifications being known to those skilled in the art.

FAB-MS(+): m/z 420 (M)+

1H-NMR(CDCl3) δ1.28(3H,d,J=7.3 Hz), 3.85(1H,q,J=7.3 Hz), 4.31(1H,d,J=14.2 Hz), 4.56(1H,d,J=14.2 Hz), 5.78 (1H,s), 6.92–7.60(4H,m), 7.62–7.72(3H,m), 7.75(2H,d,J=8.6 Hz), 8.01(2H,d,J=8.6 Hz)

EXAMPLE 7

Preparation of (2R,3R)-3-[4-(4-cyanophenyl) thiazol-2-yl)]-2-(3,4-difluorophenyl)-1-(1H-1,2,4-triazole-1-yl)-butan-2-ol This compound was synthesized by modifying the procedure of Example 4 or 5, such modifications being known to those skilled in the art.

FAB-MS(+): m/z 437 (M)+

1H-NMR(CDCl3) δ1.28(3H,d,J=6.9 Hz),3.83(1H,q,J=6.9 Hz),4.30,4.55(2H,ABq,J=14.4 Hz),5.89(1H,s),6.96~7.00 (1H,m),7.06~7.12(1H,m),7.18~7.27(1H,m),7.63(1H,s), 7.78)1H,s),7.79(1H,s),7.75,8.01(4H,ABq,J=8.4 Hz)

Example A

Dry ampoules for intramuscular administration:

A lyophilizate of 0.5 g 1-[(2R,3R)-3-[4-(4-cyanophenyl) thiazol-2-yl]-2-(2,5-difluorophenyl)-2-hydroxybutyl]-4-[3,5-dimethyl-4-[(methylamino)acetoxy]benzyl]-1H-[1,2,4] triazol-4-ium chloride hydrochloric acid salt is prepared in the usual manner and filled into an ampoule. Prior to the administration the lyophilizate is treated with 2.5 ml of a 2% aqueous lidocaine hydrochloride solution.

Example B

Hard gelatin capsules each containing the following ingredients were manufactured in the conventional manner per se:

| | |
|---|---|
| 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium chloride hydrochloric acid salt | 100 mg |
| Lactose | 56 mg |
| Crystalline Cellulose | 30 mg |
| Silicic acid, Light Anhydrous | 10 mg |
| Talc | 3 mg |
| Magnesium stearate | 1 mg |
| Total | 200 mg |

Example C

Tablets each containing the following ingredients were manufactured in the conventional manner per se:

| | |
|---|---|
| 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium chloride hydrochloric acid salt | 100 mg |
| Lactose | 60 mg |
| Corn starch | 20 mg |
| Sodium Starch Glycolate | 10 mg |
| Polyvinylpyrrolidone | 6 mg |
| Talc | 3 mg |
| Magnesium stearate | 1 mg |
| Total | 200 mg |

Example D

Hard gelatin capsules each containing the following ingredients were manufactured in the conventional manner per se:

| | |
|---|---|
| (2R,3R)-3-[4-(4-Cyanophenyl)thiazol-2-yl)]-2-(2,5-difluorophenyl)-1-(1H-1,2,4,-traizol-1-yl)-butan-2-ol, | 100 mg |
| Lactose | 56 mg |
| Crystalline cellulose | 30 mg |
| Silicic acid, light anhydrous | 10 mg |
| Talc | 3 mg |
| Magnesium stearate | 1 mg |
| Total | 200 mg |

Example E

Tablets each containing the following ingredients were manufactured in the conventional manner per se:

| | |
|---|---|
| (2R,3R)-3-[4-(4-Cyanophenyl)thiazol-2-yl)]-2-(2,5-difluorophenyl)-1-(1H-1,2,4,-traizol-1-yl)-butan-2-ol, | 100 mg |
| Lactose | 60 mg |
| Corn starch | 20 mg |
| Sodium starch glycolate | 10 mg |
| Polyvinylpyrrolidone | 6 mg |
| Talc | 3 mg |
| Magnesium stearate | 1 mg |
| Total | 200 mg |

What is claimed is:

1. Compounds of the formula I

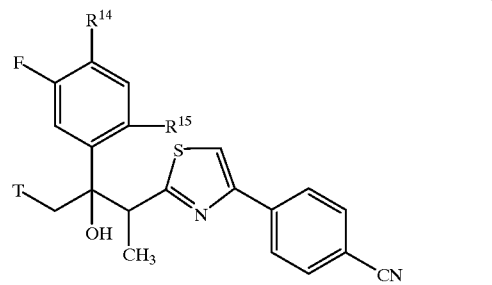

wherein $R^{14}$, $R^{15}$ are each independently hydrogen or fluorine,

T is a group of the formula:

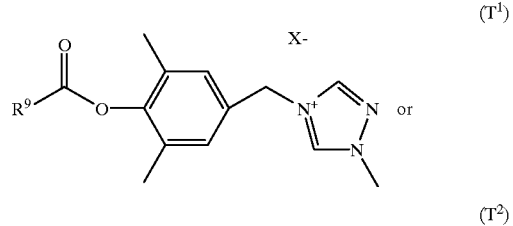

wherein $R^9$ is pyrrolidinyl or a group A—NH—B—,

A is hydrogen or straight-chain or branched $C_1$–$C_5$ alkyl;

B is straight-chain or branched $C_1$–$C_4$ alkylene, —CH$_2$—CONH—CH$_2$ or —CH$_2$CH$_2$CH$_2$—CH(NH$_2$); and $X^-$ is a pharmaceutically acceptable anion;

and pharmaceutically acceptable salts of said compounds, and hydrates and solvates of the compounds of formula I and the salts thereof.

2. A compound I' as claimed in claim 1 wherein T is the group $T^1$

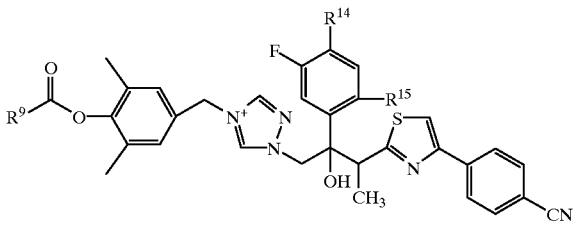

wherein
$R^{14}$, $R^{15}$ are each independently hydrogen or fluorine,
$R^9$ is pyrrolidinyl or a group A—NH—B—,
  A is hydrogen or straight-chain or branched $C_1$-$C_5$ alkyl;
  B is straight-chain or branched $C_1$-$C_4$ alkylene, —$CH_2$—CONH—$CH_2$ or —$CH_2CH_2CH_2$—CH($NH_2$), and
$X^-$ is a pharmaceutically acceptable anion;
and pharmaceutically acceptable salts of said compounds, and hydrates and solvates of the compounds of formula I and the salts thereof.

3. A compound as in claim 1, wherein:
$R^9$ is selected from the consisting of pyrrolidinyl, aminomethyl, methylaminomethyl and ethylaminomethyl,
$R^{14}$ and $R^{15}$ are H or F, or $R^{14}$ is H and $R^{15}$ is F, and
$X^-$ is $Br^-$ or $Cl^-$.

4. A compound according to claim 1 which is 1-[(2R,3R)-3-[4-(4-cyanophenyl)-thiazol-2-yl]-2-(2,4,5-trifluorophenyl)-2-hydroxybutyl]-4-[(S)-3,5-dimethyl-4-(pyrrolidine-2-carbonyloxy)-benzyl]-1H-[1,2,4]triazol-4-ium bromide, and pharmaceutically acceptable salts thereof.

5. A compound according to claim 1 which is 1-[(2R,3R)-3-[4-(4-cyanophenyl)-thiazol-2-yl]-2-(2,5-difluorophenyl)-2-hydroxybutyl]-4-[(S)-3,5-dimethyl-4-(pyrrolidine-2-carbonyloxy)-benzyl]-1H-[1,2,4]triazol-4-ium bromide, and pharmaceutically acceptable salts thereof.

6. A compound according to claim 1 which is 1-[(2R,3R)-3-[4-(4-cyanophenyl)-thiazol-2-yl]-2-(3-fluorophenyl)-2-hydroxybutyl]-4-[(S)-3,5-dimethyl-4-(pyrrolidine-2-carbonyloxy)-benzyl]-1H-[1,2,4]triazol-4-ium bromide, and pharmaceutically acceptable salts thereof.

7. A compound according to claim 1 which is (2R,3R)-4-(4-amninoacetoxy-3,5-dimethylbenzyl)-1-[3-[4-(4-cyanophenyl)thiazol-2-yl]-2-(2,4,5-trifluorophenyl)-2-hydroxybutyl]-1H-[1,2,4]triazol-4-ium bromide, and pharmaceutically acceptable salts thereof.

8. A compound according to claim 1 which is (2R,3R)-4-(4-aminoacetoxy-3,5-dimethylbenzyl)-1-[3-[4-(4-cyanophenyl)thiazol-2-yl]-2-(2,5-difluorophenyl)-2-hydroxybutyl]-1H-[1,2,4]triazol-4-ium bromide, and pharmaceutically acceptable salts thereof.

9. A compound according to claim 1 which is (2R,3R)-4-(4-aminoacetoxy-3,5-dimethylbenzyl)-1-[3-[4-(4-cyanophenyl)thiazol-2-yl]-2-(3-fluorophenyl)-2-hydroxybutyl]-1H-[1,2,4]triazol-4-ium bromide, and pharmaceutically acceptable salts thereof.

10. A compound according to claim 1 which is 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide, and pharmaceutically acceptable salts thereof.

11. A compound according to claim 1 which is 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide, and pharmaceutically acceptable salts thereof.

12. A compound according to claim 1 which is 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide, and pharmaceutically acceptable salts thereof.

13. A compound according to claim 1 which is (2R,3R)-1-[3-[4-(4-cyanophenyl)thiazol-2-yl]-2-(2,4,5-trifluorophenyl)-2-hydroxybutyl]-4-[4-[(ethylamino)-acetoxy]-3,5-dimethylbenzyl]-1H-[1,2,4]triazol-4-ium bromide, and pharmaceutically acceptable salts thereof.

14. A compound according to claim 1 which is (2R,3R)-1-[3-[4-(4-cyanophenyl)thiazol-2-yl]-2-(2,5-difluorophenyl)-2-hydroxybutly]-4-[4-[(ethylamino)-acetoxy]-3,5-dimethylbenzyl]-1H-[1,2,4]triazol-4-ium bromide, and pharmaceutically acceptable salts thereof.

15. A compound according to claim 1 which is 1-[(2R,3R)-3-[4-(4-cyanophenyl)thiazol-2-yl]-2-(3-fluorophenyl)-2-hydroxybutyl]-4-[3,5-dimethyl-4-[(ethylamino)-acetoxy]-benzyl]-1H-[1,2,4]triazol-4-ium bromide, and pharmaceutically acceptable salts thereof.

16. A compound according to claim 1 which is 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium chloride, and pharmaceutically acceptable salts thereof.

17. A compound according to claim 1 which is 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium chloride, and pharmaceutically acceptable salts thereof.

18. A compound according to claim 1 which is 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium chloride, and pharmaceutically acceptable salts thereof.

19. A compound according to claim 1 which is 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide hydrobromic acid salt.

20. A compound according to claim 1 which is 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide hydrobromic acid salt.

21. A compound according to claim 1 which is 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide hydrobromic acid salt.

22. A compound according to claim 1 which is 1-[(2R,3R)-3-[4-(4-cyanophenyl)thiazol-2-yl]-2-(2,4,5-trifluorophenyl)-2-hydroxybutyl]-4-[3,5-dimethyl-4-[(methylamino)acetoxy]benzyl]-1H-[1,2,4]triazol-4-ium bromide hydrochloric acid salt.

23. A compound according to claim 1 which is 1-[(2R,3R)-3-[4-(4-cyanophenyl)thiazol-2-yl]-2-(2,5-difluorophenyl)-2-hydroxybutyl]-4-[3,5-dimethyl-4-[(methylamino)acetoxy]benzyl]-1H-[1,2,4]triazol-4-ium bromide hydrochloric acid salt.

24. A compound according to claim 1 which is 1-[(2R,3R)-3-[4-(4-cyanophenyl)thiazol-2-yl]-2-(3-fluorophenyl)-2-hydroxybutyl]-4-[3,5-dimethyl-4-[(methylamino)acetoxy]benzyl]-1H-[1,2,4]triazol-4-ium bromide hydrochloric acid salt.

25. A compound II as claimed in claim 1 wherein T is the group $T^2$

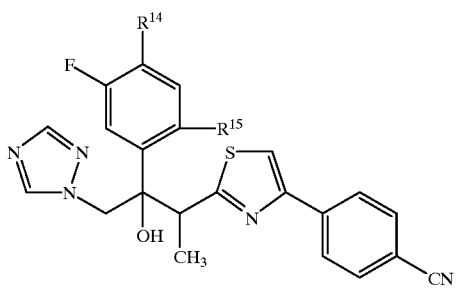

wherein $R^{14}$, $R^{15}$ are each independently hydrogen or fluorine.

26. A compound as in claim 1 wherein $R^{14}$ and $R^{15}$ are H or F.

27. A compound as in claim 1 wherein $R^{14}$ is H and $R^{15}$ is F.

28. A compound as in claim 3 wherein $R^{14}$ and $R^{15}$ are H or F.

29. A compound as in claim 3 wherein $R^{14}$ is H and $R^{15}$ is F.

30. A compound as in claim 25 wherein $R^{14}$ and $R^{15}$ are H or F.

31. A compound as in claim 25 wherein $R^{14}$ is H and $R^{15}$ is F.

32. The compound according to claim 25 which is (2R,3R)-3-[4-(4-cyanophenyl)thiazol-2-yl)]-1-(1H-1,2,4-triazol-1-yl)-2-(2,4,5-trifluorophenyl)-butan-2-ol.

33. The compound according to claim 25 which is (2R,3R)-3-[4-(4-cyanophenyl)thiazol-2-yl)]-2-(2,5-difluorophenyl)-1-(1H-1,2,4-triazol-1-yl)-butan-2-ol.

34. The compound according to claim 25 which is 2R,3R)-3-[4-(4-cyanophenyl)thiazol-2-yl)]-2-(3-fluorophenyl)-1-(1H-1,2,4-triazole-1-yl)-butan-2-ol.

35. A process for the manufacture of a compound of formula I'

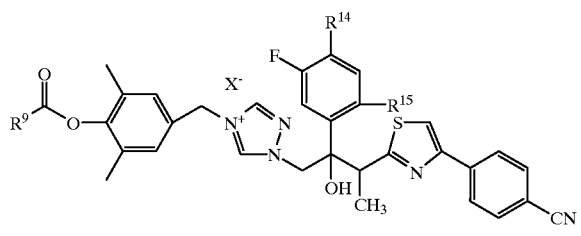

wherein $R^{14}$, $R^{15}$ are each independently hydrogen or fluorine, $R^9$ is pyrrolidinyl or a group A—NH—B—,
  A is hydrogen or straight-chain or branched $C_1$–$C_5$ alkyl;
  B is straight-chain or branched $C_1$–$C_4$ alkylene, —CH$_2$—CONH—CH$_2$ or —CH$_2$CH$_2$CH$_2$—CH(NH$_2$), and X⁻ is a pharmaceutically acceptable anion, comprising reacting an azole compound of formula II

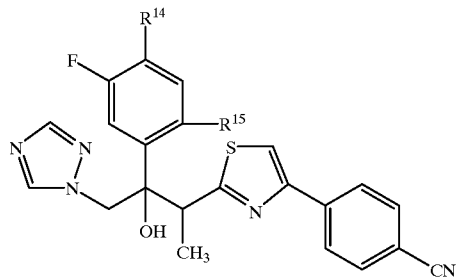

wherein $R^{14}$, $R^{15}$ are each independently hydrogen or fluorine, with a compound of formula (III),

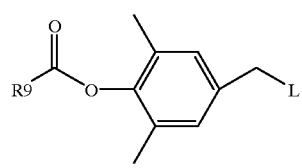

wherein $R^9$ is pyrrolidinyl or a group A—NH—B—,
  A is hydrogen or straight-chain or branched $C_1$–$C_5$ alkyl;
  B is straight-chain or branched $C_1$–$C_4$ alkylene, —CH$_2$—CONH—CH$_2$ or —CH$_2$CH$_2$CH$_2$—CH(NH$_2$), and an amino group present in $R^9$ may be in protected form;

L is a leaving group; and

X⁻ is a pharmaceutically acceptable anion;

followed if necessary by removal of a protecting group and/or if desired by salt formation.

36. A process for the manufacture of a compound of formula II as in claim 25, having the 2R,3R configuration, which process comprises:

(a) reacting 4-[(2R)-2-(3,4,5,6-tetrahydro-2H-pyran-2-yloxy)propionyl]morpholine with a compound of the formula (1),

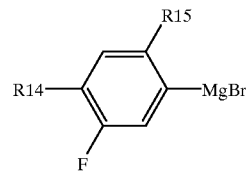

wherein $R^{14}$ and $R^{15}$ are each independently hydrogen or fluorine,

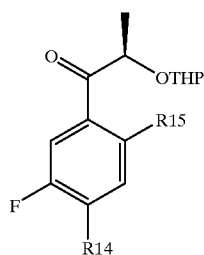
(2)

followed by (b) reacting a compound of the formula (2),
   wherein $R^{14}$ and $R^{15}$ are the same as defined above, with trimethyl sulfoxonium iodide, followed by (c) reacting a compound of the formula (3),

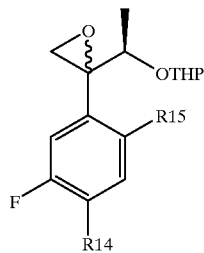
(3)

in which $R^{14}$ and $R^{15}$ are the same as defined above, with triazole in the presence of sodium hydride, followed by (d) reacting a compound of the formula (4)

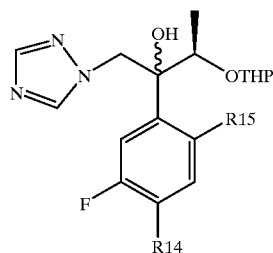
(4)

wherein $R^{14}$ and $R^{15}$ are the same as defined above, with aqueous hydrochloric acid solution or pyridinium p-toluenesulfonate, followed by (e) reacting a compound of the formula (5),

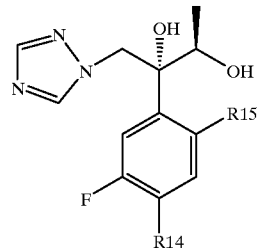
(5)

wherein $R^{14}$ and $R^{15}$ are the same as defined above, with mesyl chloride in the presence of an organic base, then with sodium methoxide, followed by (f) reacting a compound of the formula (6)

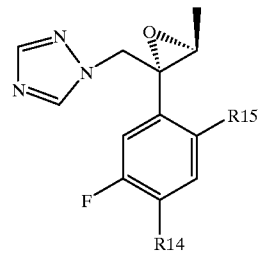
(6)

wherein $R^{14}$ and $R^{15}$ are the same as defined above, with acetone cyanohydrin in the presence of lithium hydride or trimetylsilyl cyanide in the presence of magnesium oxide, followed by (g) reacting a compound of the formula (7),

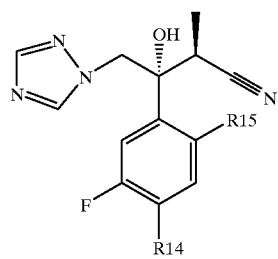
(7)

wherein $R^{14}$ and $R^{15}$ are the same as defined above, with dithiophosphoric acid O,O-diethyl ester, followed by (h) reacting a compound of the formula (8),

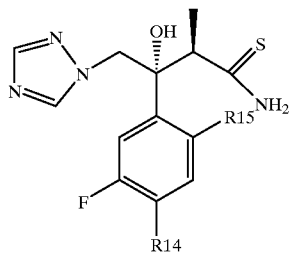
(8)

wherein $R^{14}$ and $R^{15}$ are the same as defined above, with 2-bromo-4'-cyanoacetophenone.

37. A method of treating fungal infections comprising administering a compound of the formula I:

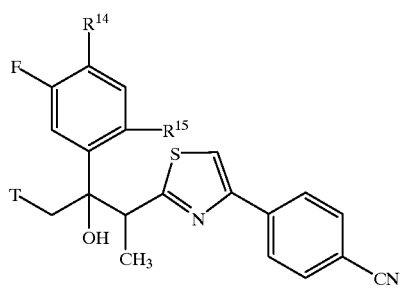
I wherein
$R^{14}$, $R^{15}$ are each independently hydrogen or fluorine,
T is a group of the formula:

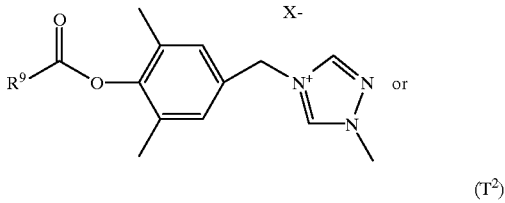
(T¹)

(T²)

wherein
$R^9$ is pyrrolidinyl or a group A—NH—B—,
A is hydrogen or straight-chain or branched $C_1$–$C_5$ alkyl;
B is straight-chain or branched $C_1$–$C_4$ alkylene, —$CH_2$—CONH—$CH_2$ or —$CH_2CH_2CH_2$—CH($NH_2$); and
$X^-$ is a pharmaceutically acceptable anion;

as well as pharmaceutically acceptable salts of said compounds, and hydrates and solvates of the compounds of formula I and the salts thereof in an amount effective for the treatment or prevention of fungal infections.

* * * * *

UNITED STATES PATENT AND TRADEMARK OFFICE
CERTIFICATE OF CORRECTION

PATENT NO.   : 6,300,353 B1
DATED        : October 9, 2001
INVENTOR(S)  : Hayase et al.

Page 1 of 1

It is certified that error appears in the above-identified patent and that said Letters Patent is hereby corrected as shown below:

Column 35, claim 2,
Lines 1-13, formula I'

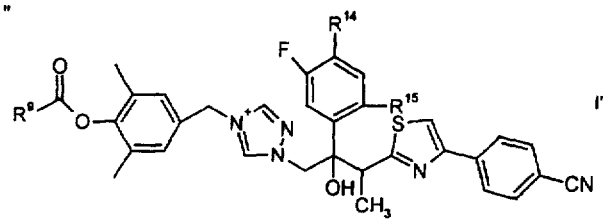

should read

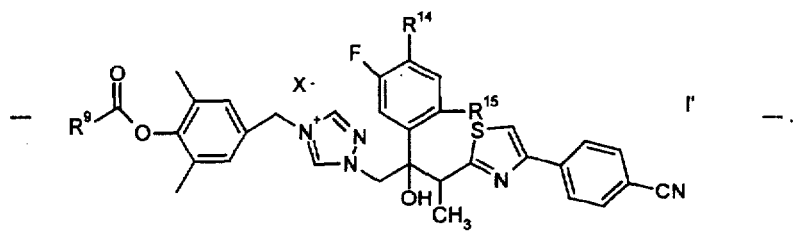

Signed and Sealed this

Twenty-sixth Day of March, 2002

Attest:

JAMES E. ROGAN
Attesting Officer    Director of the United States Patent and Trademark Office